United States Patent [19]

Gorman

[11] Patent Number: 5,024,939
[45] Date of Patent: Jun. 18, 1991

[54] TRANSIENT EXPRESSION SYSTEM FOR PRODUCING RECOMBINANT PROTEIN

[75] Inventor: Cornelia M. Gorman, San Francisco, Calif.

[73] Assignee: Genentech, Inc., South San Francisco, Calif.

[21] Appl. No.: 101,712

[22] Filed: Sep. 25, 1987

Related U.S. Application Data

[63] Continuation-in-part of Ser. No. 71,674, Jul. 9, 1987, abandoned, which is a continuation-in-part of Ser. No. 907,185, Sep. 12, 1986, abandoned.

[51] Int. Cl.$^5$ ............................................. C12N 15/67
[52] U.S. Cl. .................................. 435/69.1; 435/172.3
[58] Field of Search ........................ 435/68, 172.3, 235, 435/320, 69.1; 935/32, 34, 27, 56

[56] References Cited

U.S. PATENT DOCUMENTS

| | | | |
|---|---|---|---|
| 4,599,308 | 7/1986 | Hamer et al. | 435/69.1 |
| 4,738,922 | 4/1988 | Haseltine | 435/69.1 |
| 4,740,461 | 4/1988 | Kaufmen | 435/69.1 |
| 4,745,069 | 5/1988 | Mayne et al. | 435/320 |
| 4,775,630 | 10/1988 | Tibbetts et al. | 435/320 |

FOREIGN PATENT DOCUMENTS

| | | |
|---|---|---|
| 0073656 | 3/1983 | European Pat. Off. . |
| 0173177 | 3/1986 | European Pat. Off. . |
| 0232544 | 8/1987 | European Pat. Off. . |
| 0260148 | 3/1988 | European Pat. Off. . |
| 8505636 | 12/1985 | PCT Int'l Appl. . |
| 8605514 | 9/1986 | PCT Int'l Appl. . |
| 8703619 | 6/1987 | PCT Int'l Appl. . |
| 87/03904 | 7/1987 | PCT Int'l Appl. . |
| 8703905 | 7/1987 | PCT Int'l Appl. . |

OTHER PUBLICATIONS

ATCC Catalogue of Cell Lines and Hybridomas, 6th edition, 1988, p. 151.
Vasudevachari, 1987 (Mar.), 7(3)1063–1069, Model T Cell. Biology.
Imperiale, M. J., 1983, Cell, 35:127–136.
Pasleau, F. et al., 1985, Gene, 38:227–232.
Boshart, M. et al., Cell, 41:521–530, Jun. 1985.
Mory, Y. et al., 1986, DNA, 5(3):181–193.
Mount, S. M. et al., Nucleic Acids Research, 10(2)459–472, 1982.
Hamer et al., 1979, Cell, 18:1299–1302.
Cohen, J. B. et al., 1983, Embo J., 2:2013–2018.
Alwine, J. C., 1985, Mol. Cell. Biol., 5(5)1034–1042.
Ruether, J. E. et al., 1986, Mol. Cell. Biol., 6(1)123–133.
Svensson, C. et al. (1989), Mol. Cell. Biol., 4(4), 736–742.
Babiss et al., Mol. & Cell. Biol., 5:2552–2558 (1985).
Babich et al., Mol. & Cell. Biol., 3(7):1212–1221 (1983).
Babiss & Ginsberg, J. Virol., 50(1):202–212 (1984).
Roizman & Batterson, Virology, Fields et al. (ed), Raven Press (1985), pp. 497–526.
Whittaker et al., Mol. & Cell. Biol., 4(1):110–116 (1984).
Borelli et al., Nature, 321:249–251 (1986).
Velcich & Ziff, Cell, 40:705–716, (1985).
Hen et al., Science, 230:1391–1394, (1985).
Thimmappaya et al., Cell, 31:543–551, (1982).
Kaufman et al., Mol. Cell. Biol., 2:1304–1319, (1982).
Kaufman et al., J. Mol. Biol., 159:601–621, (1982).
Wong et al., Science, 228:810–815, (1985).
Akusjarvi et al., Nature, 292:420–426, (1981).
Akusjarvi et al., Mol. Cell. Biol., 7(1):549–551, (1987).
Alwine, J. C., Mol. Cell. Biol., 5(5):1034–1042, (1985).
(List continued on next page.)

Primary Examiner—Richard A. Schwartz
Attorney, Agent, or Firm—Max D. Hensley; Robert H. Benson

[57] ABSTRACT

A method is described for transient production of a desired heterologous protein comprising: transfecting a eukaryotic host cell with a vector producing a transactivating protein; transfecting the eukaryotic host cell with an expression vector comprising a stabilizing sequence downstream of a promoter and upstream of a DNA encoding the desired heterologous protein and a polyadenylation sequence downstream of which is a transcription terminatein site; culturing the transfected eukaryotic host cell under conditions favorable for production of said desired heterologous protein; and, recovering the desired protein in useful amounts within about one day to about fourteen days of transfection.

27 Claims, 21 Drawing Sheets

OTHER PUBLICATIONS

Babiss et al., J. Virol., 46(2):454–465, (1983).
Braun et al., Biochem. Biophys. Res. Comm., 149(1):125–132, (1987).
Burke et al., J. Biol. Chem., 261(27):12574–12578, (1986).
Blair et al., J. Virol., 61(8):2499–2508, (1987).
Bhat et al., J. Virol., 56(3):750–756, (1985).
Bos et al., EMBO J., 2(1):73–76, (1983).
Bothwell et al., Cell, 24:625–637, (1981).
Borrelli et al., Nature, 312:608–612, (1984).
Clark et al., P.N.A.S. USA, 81:2543–2547, (1984).
Chen et al., J. Virol., 48:492–502, (1983).
Crick, F., Science, 204:264–271, (1979).
Sassone-Corsi et al., Nature, 313:458–463, (1985).
Carlock et al., Nature, 294:572–574, (1981).
Chu et al., Nature, 289:378–382, (1981).
DiMaio et al., J. Mol. Biol., 156:531–548, (1982).
Fisher et al., Thromb. Res., 48:89–99, (1987).
Foecking et al., Gene, 45:101–105, (1986).
Gaynor et al., P.N.A.S. USA, 81:1193–1197, (1984).
Gaynor et al., Cell, 33:683–693, (1983).
Ghosh et al., P.N.A.S. USA, 78(3):1386–1390, (1981).
Gruss et al., P.N.A.S. USA, 76(9):4317–4321, (1979).
Graham et al., J. Gen. Virol., 36:59–74, (1977).
Gorman et al., Science, 221:551–553, (1983).
Gorman et al., Cell, 42:519–526, (1985).
Gluzman, Y., Cell, 23:175–182, (1981).
Gething et al., Nature, 293:620–625, (1981).
Greenspan et al., Mol. Cell. Biol., 5(8):1894–1900, (1985).
Hall et al., J. Mol. App. Gen., 2:101–109, (1983).
Hoefler et al., Cell, 41:955–963, (1985).
Hamer et al., Cell, 21:697–708, (1980).
Hamer et al., Nature, 281:35–40, (1979).
Kenten et al., DNA, 5(3):257–262, (1986).
Kitajewski et al., Cell, 45:195–200, (1986).
Kozak M., Cell, 44:283–292, (1986).
Loeken et al., Mol. Cell. Biol., 6(6):2020–2026, (1986).
Lewis et al., Nature, 317:172–175, (1985).
Lewis et al., P.N.A.S. USA, 80:7065–7069, (1983).
Lamins et al., P.N.A.S. USA, 79:6453–6457, (1982).
Liu et al., DNA, 1(3):213–221, (1982).
Leung et al., Nature, 330:537–543, (1987).
Lebkowski et al., Nature, 317:169–171, (1985).
Liu et al., Nature, 309:82–85, (1984).
Lusky et al., Nature, 293:79–81, (1981).
Lupton et al., Mol. Cell. Biol., 5(10):2533–2542, (1985).
Mulligan et al., Science, 209:1422–1427, (1980).
Miyamato et al., EMBO J., 4(13A):3563–3570, (1985).
Mather et al., Ann. N.Y. Acad. Sci., pp. 44–68, (1982).
Mather, J. P., IN VITRO, 18(12):990–996, (1982).
Mulligan et al., Nature, 277:108–114, (1979).
Nevins et al., J. Mol. Biol., 130:493–506, (1979).
Nevins et al., Nature, 290:113–118, (1981).
Pavirani et al., Biochem. Biophys. Res. Comm., 145(1):234–240, (1987).
Prives et al., Mol. Cell. Biol., 3(11):1958–1966, (1983).
Roberts et al., J. Virol, 56(2):404–413, (1985).
Rio et al., Science, 227:23–28, (1985).
Reichel et al., Nature, 313:196–200, (1985).
Sarnow et al., J. Virol., 49(3):692–700, (1984).
Seed et al., P.N.A.S. USA, 84:3365–3369, (1987).
Svensson et al., EMBO J., 4(4):957–964, (1985).
Svensson et al., P.N.A.S. USA, 83:4690–4694, (1986).
Stinski et al., J. Virol., 46:1–14, (1983).
Stinski et al., J. Virol., 55(2):431–441, (1985).
Spangler et al., Science, 237:1044–1046, (1987).
Solnick, D., EMBO J., 2(6):845–851, (1983).
Sharp, P., Cell, 23:643–646, (1981).
Shaw et al., Cell, 22:905–916, (1980).
Singh et al., Nature, 314:553–556, (1985).
Simon et al., Mol. Cell. Biol., 7(8):2884–2890, (1987).
Sugden et al., Mol. Cell. Biol., 5(2):410–413, (1985).
Svensson et al., Mol. Cell. Biol., 4(4):736–742, (1984).
Treisman et al., P.N.A.S. USA, 80:7428–7432, (1983).
Treisman et al., Nature, 292:595–600, (1981).
Whittaker et al., Mol. Cell. Biol., 4(1):110–116, (1984).
Wigler et al., Cell, 16:777–785, (1979).
Walker et al., Nature, 306:557–561, (1983).
Wood et al., Nature, 312:330–337, (1984).
Zerler et al., Mol. Cell. Biol., 6(3):887–899, (1986).
Perez-Infante et al., Exp. Cell. Res., 142:325–332, (1982).

Fig.10.

```
     aluI
     sacI
     hgiAI
     bsp1286
     banII
     taqI                      speI
  1  TTCGAGCTCG CCCGACATTG ATTATTGACT AGTTATTAAT AGTAATCAAT TACGGGGTCA
     AAGCTCGAGC GGGCTGTAAC TAATAACTGA TCAATAATTA TCATTAGTTA ATGCCCCAGT
     from pPMLCMV beginning to HindIII, enhancers and promoter scrFI
                                                           bglI bstNI
                                                                sau96I
                              thaI                              haeIII
 61  TTAGTTCATA GCCCATATAT GGAGTTCCGC GTTACATAAC TTACGGTAAA TGGCCCGCCT
     AATCAAGTAT CGGGTATATA CCTCAAGGCG CAATGTATTG AATGCCATTT ACCGGGCGGA ahaII
                             aatII
121  GGCTGACCGC CCAACGACCC CCGCCCATTG ACGTCAATAA TGACGTATGT TCCCATAGTA
     CCGACTGGCG GGTTGCTGGG GGCGGGTAAC TGCAGTTATT ACTGCATACA AGGGTATCAT ahaII
                      aatII                                bglI
181  ACGCCAATAG GGACTTTCCA TTGACGTCAA TGGGTGGAGT ATTTACGGTA AACTGCCCAC
     TGCGGTTATC CCTGAAAGGT AACTGCAGTT ACCCACCTCA TAAATGCCAT TTGACGGGTG ahaII
     rsaI              ndeI        rsaI            aatII
241  TTGGCAGTAC ATCAAGTGTA TCATATGCCA AGTACGCCCC CTATTGACGT CAATGACGGT
     AACCGTCATG TAGTTCACAT AGTATACGGT TCATGCGGGG GATAACTGCA GTTACTGCCA bglI
     sau96I scrFI           nlaIII
     haeIII bstNI           rsaI                                     rsaI
301  AAATGGCCCG CCTGGCATTA TGCCCAGTAC ATGACCTTAT GGGACTTTCC TACTTGGCAG
     TTTACCGGGC GGACCGTAAT ACGGGTCATG TACTGGAATA CCCTGAAAGG ATGAACCGTC nlaIII
                              styI     sfaNI
            snaBI             ncoI hphI                      rsaI
361  TACATCTACG TATTAGTCAT CGCTATTACC ATGGTGATGC GGTTTTGGCA GTACATCAAT
     ATGTAGATGC ATAATCAGTA GCGATAATGG TACCACTACG CCAAAACCGT CATGTAGTTA ahaII
              hinfI                                             aatII
421  GGGCGTGGAT AGCGGTTTGA CTCACGGGGA TTTCCAAGTC TCCACCCCAT TGACGTCAAT
     CCCGCACCTA TCGCCAAACT GAGTGCCCCT AAAGGTTCAG AGGTGGGGTA ACTGCAGTTA nlaIV
         banI
481  GGGAGTTTGT TTTGGCACCA AAATCAACGG GACTTTCCAA AATGTCGTAA CAACTCCGCC
     CCCTCAAACA AAACCGTGGT TTTAGTTGCC CTGAAAGGTT TTACAGCATT GTTGAGGCGG
```

```
                                                                    aluI
                                                                    sacI
                                                                    hgiAI
                                                                    bsp1286
        hgaI                        rsaI       mnlI                 banII
541 CCATTGACGC AAATGGGCGG TAGGCGTGTA CGGTGGGAGG TCTATATAAG CAGAGCTCGT
    GGTAACTGCG TTTACCCGCC ATCCGCACAT GCCACCCTCC AGATATATTC GTCTCGAGCA scrFI
        sau3AI          hgaI
        dpnI   bstNI   ahaII  fokI                  mnlI      mboII
601 TTAGTGAACC GTCAGATCGC CTGGAGACGC CATCCACGCT GTTTTGACCT CCATAGAAGA
    AATCACTTGG CAGTCTAGCG GACCTCTGCG GTAGGTGCGA CAAAACTGGA GGTATCTTCT
              Begin RNA scrFI
        sau96I                ncil
        avaII                 haeIII
        nlaIV                 xmaIII
        scrFI                 eaeI
        ncil                  fnu4HI
        mspI    sau3AI mnlI thaI mspI
        hpaII   dpnI   bglI sacII hpaII             thaI  hinfI
661 CACCGGGACC GATCCAGCCT CCGCGGCCGG GAACGGTGCA TTGGAACGCG GATTCCCCGT
    GTGGCCCTGG CTAGGTCGGA GGCGCCGGCC CTTGCCACGT AACCTTGCGC CTAAGGGGCA bstXI
                                              sau96I
              rsaI       hinfI      haeIII    styI
721 GCCAAGAGTG ACGTAAGTAC CGCCTATAGA GTCTATAGGC CCACCCCCTT GGCTTCTTAT
    CGGTTCTCAC TGCATTCATG GCGGATATCT CAGATATCCG GGTGGGGGAA CCGAAGAATA haeI
                                               eaeI
    sau3AI                                     balI
    dpnI                                       sau3AI
    xhoII           aluI                       dpnI
    nlaIV           ddeI       mnlI            xhoII
    bamHI   rsaI hindIII                       bglII haeIII
781 GCGACGGATC CCGTACTAAG CTTGAGGTGT GGCAGGCTTG AGATCTGGCC ATACACTTGA
    CGCTGCCTAG GGCATGATTC GAACTCCACA CCGTCCGAAC TCTAGACCGG TATGTGAACT
              IgE synthetic 100mer fnu4HI
                                                              bbvI
        fokI                                                  pstI
841 GTGACAATGA CATCCACTTT GCCTTTCTCT CCACAGGTGT CCACTCCCAC GTCCAACTGC
    CACTGTTACT GTAGGTGAAA CGGAAAGAGA GGTGTCCACA GGTGAGGGTG CAGGTTGACG
                                                              PstI-ClaI
                                                              converter claI
              sau3AI
              dpnI
              pvuI
    aluI    taqI taqI
901 AGCTCGGTTC GATCGATAA               Fig.10 (cont.)
    TCGAGCCAAG CTAGCTATT
```

Fig.11.

```
                                                                     nlaIv
                                                                     scrFI
                                                                     bstNI
    xmnI
  1 GAATTAATTC TGTGGAATGT GTGTCAGTTA GGGTGTGGAA AGTCCCCAGG CTCCCCAGCA
    CTTAATTAAG ACACCTTACA CACAGTCAAT CCCACACCTT TCAGGGGTCC GAGGGGTCGT nsiI
           avaIII                                scrFI            scrFI
           nlaIII                                bstNI            bstNI
           sphI sfaNI
 61 GGCAGAAGTA TGCAAAGCAT GCATCTCAAT TAGTCAGCAA CCAGGTGTGG AAAGTCCCCA
    CCGTCTTCAT ACGTTTCGTA CGTAGAGTTA ATCAGTCGTT GGTCCACACC TTTCAGGGGT nlaIv                           nsiI
                                    avaIII
                                    nlaIII
                                    sphI sfaNI
121 GGCTCCCCAG CAGGCAGAAG TATGCAAAGC ATGCATCTCA ATTAGTCAGC AACCATAGTC
    CCGAGGGGTC GTCCGTCTTC ATACGTTTCG TACGTAGAGT TAATCAGTCG TTGGTATCAG styI
                                                                     ncoI
             fokI
181 CCCGCCCCTAA CTCCGCCCAT CCCGCCCCTA ACTCCGCCCA GTTCCGCCCA TTCTCCGCCC
    GGCGGGGATT GAGGCGGGTA GGGCGGGGAT TGAGGCGGGT CAAGGCGGGT AAGAGGCGGG fnu4HI
                                       sfiI
                                       haeIII          ddeI
                                       haeIII bglI    haeIII
    nlaIII                             mnlI mnlI      mnlI mnlI       aluI
241 CATGGCTGAC AGTGAGGAGG TATTTATGCA GAGGCCGAGG CCGCCCTCGC CTCTGAGCTA
    GTACCGACTG TCACTCCTCC ATAAATACGT CTCCGGCTCC GGCGGAGCCG GAGACTCGAT styI
                             haeIII
               stuI
               haeI
         mnlI    mnlI avrII                          aluI ecoRI sau96I
301 TTCCAGAAGT AGTGAGGAGG CTTTTTTTGGA GGCCTAGGCT TTTGCAAAAA GCTGAATTCG
    AAGGTCTTCA TCACTCCTCC GAAAAAACCT CCGGATCCGA AAACGTTTTT CGACTTAAGC
```

```
      scrFI
      ncıI
      mspI
      hpaII                          hinfI
      haeIII                         thaI                                    rsaI
  361 GGCCGGGAAC GGTGCATTGG AACGCGGATT CCCCGTGCCA AGAGTGACGT AAGTACCGCC
      CCGGCCCTTG CCACGTAACC TTGCGCCTAA GGGGCACGGT TCTCACTGCA TTCATGGCGG
      SacI site from pAML3P
      SacII site from CMVS
                                                              sau3AI
                                                              dpnI
                                      bstXI                   xhoII        aluI
                       sau96I                                 nlaIV        ddeI    mnlI
              hinfI    haeIII    styI                         bamHI  rsaI  hindIII
  421 TATAGAGTCT ATAGGCCCAC CCCCTTGGCT TCTTATGCGA CGGATCCCGT ACTAAGCTTG
      ATATCTCAGA TATCCGGGTG GGGGAACCGA AGAATACGCT GCCTAGGGCA TGATTCGAAC
                                                                    IgE synthetic
                                                                    100mer
                       haeIII
               sau3AI
               dpnI  haeI
               xhoII eaeI                           fokI
               bglII balI                                                taqI
                                                                         claI
                                                                         sau3AI
  481 AGGTGTGGCA GGCTTGAGAT CTGGCCATGA ACTTGAGTGA CAATGACATC  CACTTTGCCT
      TCCACACCGT CCGAACTCTA GACCGGTATG TGAACTCACT  GTTACTGTAG GTGAAACGGA
                                                                         dpnI
                                                             aluI        pvuI
                                                             fnu4HI      taqI
                                                             bbvI
                                                             pstI
  541 TTCTCTCCAC AGGTGTCCAC TCCCACGTCC AACTGCAGCT CGGTTCGATC GATAA
      AAGAGAGGTG TCCACAGGTG AGGGTGCAGG TTGACGTCGA GCCAAGCTAG CTATT
                                                  PstI-ClaI converter
```

```
         aluI
         sacI
         hgiAI
         bsp1286
         banII
       taqI                            speI
  1 TTCGAGCTCG CCCGACATTG ATTATTGACT AGTTATTAAT AGTAATCAAT TACGGGGTCA
    AAGCTCGAGC GGGCTGTAAC TAATAACTGA TCAATAATTA TCATTAGTTA ATGCCCCAGT
       from pPMLCMV beginning to HindIII,enhancers and promoter scrFI
                                                          bglI bstNI
                                                               sau96I
                                  thaI                         haeIII
 61 TTAGTTCATA GCCCATATAT GGAGTTCCGC GTTACATAAC TTACGGTAAA TGGCCCGCCT
    AATCAAGTAT CGGGTATATA CCTCAAGGCG CAATGTATTG AATGCCATTT ACCGGGCGGA ahaII
                                 aatII
121 GGCTGACCGC CCAACGACCC CCGCCCATTG ACGTCAATAA TGACGTATGT TCCCATAGTA
    CCGACTGGCG GGTTGCTGGG GGCGGGTAAC TGCAGTTATT ACTGCATACA AGGGTATCAT ahaII
                       aatII                                   bglI
181 ACGCCAATAG GGACTTTCCA TTGACGTCAA TGGGTGGAGT ATTTACGGTA AACTGCCCAC
    TGCGGTTATC CCTGAAAGGT AACTGCAGTT ACCCACCTCA TAAATGCCAT TTGACGGGTG ahaII
       rsaI        ndeI       rsaI                  aatII
241 TTGGCAGTAC ATCAAGTGTA TCATATGCCA AGTACGCCCC CTATTGACGT CAATGACGGT
    AACCGTCATG TAGTTCACAT AGTATACGGT TCATGCGGGG GATAACTGCA GTTACTGCCA bglI
       sau96I scrFI               nlaIII
       haeIII bstNI               rsaI                         rsaI
301 AAATGGCCCG CCTGGCATTA TGCCCAGTAC ATGACCTTAT GGGACTTTCC TACTTGGCAG
    TTTACCGGGC GGACCGTAAT ACGGGTCATG TACTGGAATA CCCTGAAAGG ATGAACCGTC nlaIII
                       styI    sfaNI
          snaBI        ncoI hphI                               rsaI
361 TACATCTACG TATTAGTCAT CGCTATTACC ATGGTGATGC GGTTTTGGCA GTACATCAAT
    ATGTAGATGC ATAATCAGTA GCGATAATGG TACCACTACG CCAAAACCGT CATGTAGTTA
```

```
                                                            ahaII
                       hinfI                                aatII
421 GGGCGTGGAT AGCGGTTTGA CTCACGGGGA TTTCCAAGTC TCCACCCCAT TGACGTCAAT
    CCCGCACCTA TCGCCAAACT GAGTGCCCCT AAAGGTTCAG AGGTGGGGTA ACTGCAGTTA nlaIV
               banI
481 GGGAGTTTGT TTTGGCACCA AAATCAACGG GACTTTCCAA AATGTCGTAA CAACTCCGCC
    CCCTCAAACA AAACCGTGGT TTTAGTTGCC CTGAAAGGTT TTACAGCATT GTTGAGGCGG aluI
                                                             sacI
                                                             hgiAI
                                                             bsp1286
         hgaI                     rsaI      mnlI             banII
541 CCATTGACGC AAATGGGCGG TAGGCGTGTA CGGTGGGAGG TCTATATAAG CAGAGCTCGT
    GGTAACTGCG TTTACCCGCC ATCCGCACAT GCCACCCTCC AGATATATTC GTCTCGAGCA scrFI
         sau3AI         hgaI
         dpnI bstNI     ahaII fokI                mnlI        mboII
601 TTAGTGAACC GTCAGATCGC CTGGAGACGC CATCCACGCT GTTTTGACCT CCATAGAAGA
    AATCACTTGG CAGTCTAGCG GACCTCTGCG GTAGGTGCGA CAAAACTGGA GGTATCTTCT
                Begin RNA scrFI
         sau96I            ncII
         avaII             haeIII
         nlaIV             xmaIII
         scrFI             eaeI
         ncII              fnu4HI
         mspI    sau3AI mnlI thaI mspI
         hpaII   dpnI bglI sacII hpaII    hphI          thaI hinfI
661 CACCGGGACC GATCCCAGCC TCCGCGGCCG GAACGGTGA TTGGAACGCG GATTCCCCGT
    GTGGCCCTGG CTAGGGTCGG AGGCGCCGGC CCTTGCCACT AACCTTGCGC CTAAGGGGCA claI
                                             aluI         sau3AI
                                             fnu4HI       dpnI
                                             bbvI    mspI taqI taqI
         tth111I                             pstI    hpaII pvuI
721 GCCAAGAGTG ACGGTGTCCA CTCCCACGTC CAACTGCAGC TCCGGTTCGA TCGATAA
    CGGTTCTCAC TGCCACAGGT GAGGGTGCAG GTTGACGTCG AGGCCAAGCT AGCTATT
```

Fig.12(cont.)

TRANSIENT EXPRESSION SYSTEM FOR PRODUCING RECOMBINANT PROTEIN

This is a Continuation-in-Part of U.S. Ser. No. 07/071,674, filed July 9, 1987, now abandoned, which is a Continuation-in-Part of U.S. Ser. No. 06/907,185 filed Sept. 12, 1986, now abandoned.

BACKGROUND OF THE INVENTION

This invention relates to the application of recombinant DNA technology to develop an expression system capable of expressing desired proteins within about one day to about two weeks of transfection. Furthermore, the invention relates to the transformation of a host cell with an expression vector capable of generating stable cytoplasmic mRNA to express a desired protein and vectors capable of expressing trans-activating factors and/or certain translational control effectors, so as to give rise to transient production of the desired protein. The invention further relates to the transfection of selected eukaryotic cells with such vectors such that transient production of the desired protein is obtained.

Recombinant technology has recently been applied to eukaryotic cells, specifically mammalian cells were transformed with heterologous DNA coding for a selectable phenotype. Wigler, M., et al., Cell 11: 223–232 (1977). It has also been shown that eukaryotic cells can be transformed to yield transformants having heterologous DNA integrated into the chromosomal DNA of the eukaryotic cell nucleus.

Successful transformation of eukaryotic cell cultures and expression of DNA sequences coding for a desired protein has been disclosed. See for example, European Patent Publications Nos. 73,659 and 73,656. These successful transformations have utilized vectors to express complimentary DNA (cDNA's) requiring only 5' control signals such as enhancers (Gluzman, Y and Shenk, T. [eds] Enhancers and Eukaryotic Gene Expression [Cold Spring Harbor Laboratory, 1983]), promoters (Hamer, D. H. et al., Cell 21, 697 [1980]) and 3' polyadenylation sites (Proudfoot, N.J. and Brownlee, G. G., Nature 263, 211 [1976]).

In 1977 it was found that in eukaryotes the cytoplasmic mRNA is not always co-linear with the DNA. DNA sequences encoding proteins were found to be interrupted by stretches of non-coding DNA. There are long stretches of base sequence in the DNA of the gene which do not appear in the final mRNA. It was observed that the primary mRNA transcripts were "spliced" to remove the non-coding sequences, i.e. sequences which do not encode a protein. These non-coding sequences in DNA are generally referred to as introns (formerly referred to as intervening sequences) while the coding sequences are known as exons. RNA polymerase makes a primary transcript of the entire DNA, both exons and introns. This transcript was processed so that the introns were removed while at the same time the exons were all joined together in the correct order. The mechanism producing the foregoing result is referred to as "splicing."

Numerous split or spliced genes have been discovered. In fact, introns exist in virtually all mammalian and vertebrate genes and also in the genes of eukaryotic microorganisms. Introns are not limited to the coding region of a message. For example, one intron was found in the leader region of the plasminogen activator mRNA before the coding sequence in addition to multiple splice sites elsewhere in the gene. Fisher, R. et al., J. Biol. Chem. 260, 1122 (1985). There has been considerable speculation about why introns have evolved and become such a general feature of eukaryotic genes. Crick, F., Science 204, 264, 1979; and, Sharp, P. A., Cell 23, 643–646 (1981).

Given the ubiquity of introns, it is not surprising that splicing was studied in the context of recombinant technology. For example, an SV40 vector was constructed containing a rabbit β-globin cDNA, regions implicated in transcription initiation and termination, splice sites from a multipartite leader sequence located 5' to the β-globin cDNA sequence and a polyadenylation sequence. Mulligan, R. C. et al., Nature 277, 108–114 (1979). This recombinant genome, when infected into monkey kidney cells, was found to produce hybrid mRNAs containing the leader region for the 16S and 19S late RNA and the β-globin coding sequence. This hybrid mRNA produced substantial quantities of the rabbit β-globin polypeptide. Mulligan et al. discuss an experiment in which mutants lacking splicing capability failed to produce discrete mRNAs. Id. at 109.

In an attempt to establish the physiological role that RNA splicing plays in gene expression, Hamer, D. H. and Leder, P., Cell 18, 1299–1302 (1979) manipulated the location and/or presence of a splice site in SV40 recombinants transfected into monkey cells. Hamer and Leder, supra, used one splice site located within the gene encoding the desired protein or used two splice site sequences, one located 5' to and the second within the gene encoding the desired protein. They found that RNA were produced transiently by all of the viruses that retain at least one functional splice junction. They concluded that splicing is a prerequisite for stable RNA formation. Confirming that result, Gruss, P. et al. PNAS (USA), 76 4317–4321 (1979) found that construction of an SV40 mutant lacking an intervening sequence made no detectable capsid protein. These two papers suggest that RNA splicing may be important in a recombinant milieu. However, other studies abandoned splicing to express proteins using only 5' control signals such as enhancers, and promoters and 3' polyadenylation sites. In fact, recent work by Reddy, U. B. et al., Transcriptional Control Mechanisms, J. Cell. Biochem. Suppl. 10D, 154 (1986), found that the inclusion of introns in an expression vector actually reduced the amount of the desired protein expressed.

Straightforward expression using standard recombinant control signals such as enhancers, promoters and 3' polyadenylation sites cannot always be achieved. The SV40 promoter without a splice site has been used to direct expression of numerous cDNAs. (β-galactosidase, Hall, C. V. et al. J. Mol. Applied Genetics 2,; human interferon, Gray, P. W., et al., Nature 295, 503 (1982); hemagglutinin, Gething, et al. Nature 293, 620 (1981); human lecithin-cholesterol acyltransferase, McLean, J. et al., PNAS 33, 2335 (1986); DHFR, Simonsen, C. C. et al., PNAS 80, 2495 (1983); human interleukin-2, Leonard, W. T. et al., Nature 311, 626 (1984); ras-2, Capon, D. J. et al. Nature 304, 1983; src, Snyder, M. A. et al., Cell 32, 891 (1983); and hepatitis B surface antigen, Crowley, C. W. et al., Mol. Cell Biol. 3, 44–55 (1983)).

Transient expression systems have been used as tools of recombinant technology. For example, the analysis of promoter sequences, effects of enhancers, and demonstration of transcription regulation have been facilitated using transient expression systems. One well characterized transient expression system is that for chloramphenicol acetyl transferase (CAT) (Gorman, C. M. et al., Mol. Cell. Biol. 2:1044-1051 [1982]).

Various viral proteins produced in cells infected by DNA viruses are known to activate viral genes expressed during later phases of the temporally regulated lytic life cycle. (Keller, J. M. et al., Cell 36:381-389 [1984]). These proteins include simian virus 40 (SV40) T antigen, adenovirus Ela and Elb protein, the herpesvirus immediate early (IE) proteins and human and simian immunodeficiency viruses. (Benoist, C. and Chamber, P., Nature (Lond.) 290:304-310 [1981]; Hearing, P. and Shenk, T., Cell 39:653-662 [1983]; Rosen, C. et al., Nature 319, 555-559 [1986]). These proteins are the products of genes containing efficient promoters activated by cis-acting elements. Each protein may also have a trans-activating function by activating the expression of other viral genes to permit the virus to progress through its lytic cycle. A transcriptional activation function by increasing expression of other viral genes of each of these proteins has been demonstrated in its respective viral system. Since this transcriptional activation can be provided by cotransfection of a separate plasmid, this effect is referred to as "trans-activation." (Berk, A. J. et al. Cell 17:935-944 [1979]; Brady, J. et al. PNAS [USA] 81:2040-2044 [1984]; Dixon, R.A.F. and Shaffer, P. A., J. Virol. 36:189-203 [1980]; Jones, N. and Shenk. T., PNAS [USA] 76:3665-3669 [1979]). Some data using transient expression with Ela and the IE proteins indicate that these proteins may also trans-activate promoters that are not homologous to their respective viral system. (Green, M. R. et al., Cell 35:137-148 [1983]; Imperiale, M. R. et al., Cell 35:127-136 [1983]). Other data suggests that Ela suppresses some enhancers. (Borelli, E. R. et al., Nature [Lond.] 312:608-612 [1984]).

It is an object of the present invention to provide a transient expression system capable of producing a desired protein. Another object of this invention is to eliminate the time necessary to establish continuous production to obtain a desired protein. It is an object of this invention to provide useful amounts of a desired recombinant protein in about one day to two weeks after transfection. Yet another object of this invention is to provide expression vectors useful in a transient expression system. Still another object of this invention is to provide a host cell capable of being used in a transient expression system to produce a desired protein in about one day to fourteen days of transfection. Another object is to provide certain trans-activating factors and/or translational control effectors capable of enhancing the yields of a desired protein in a transient expression system by stabilizing the transfected DNA.

SUMMARY OF THE INVENTION

The objects of the present invention are accomplished by a novel method for production of a desired heterologous protein in a eukaryotic host cell comprising: constructing a first expression vector which comprises a promoter, stabilizing sequence, DNA encoding a desired heterologous protein and a polyadenylation sequence; transfecting the eukaryotic host cell with the first expression vector; transfecting the host cell with a vector producing a trans-activating protein effector; culturing the transfected host cell under conditions favorable for production of the desired protein; and, recovering the desired protein in useful amounts within about two days to about fourteen days. The method of this invention may additionally include transfection of the eukaryotic host cell with a vector capable of expressing a translational control effector. The method of this invention enables the production of useful quantities of a desired protein without having to establish continuous production. This invention provides significant advantages by providing useful amounts of a desired protein in a relatively short period of time. Accordingly, in one aspect the invention provides a method for producing, by recombinant means, a desired heterologous protein in from about one day to about fourteen days after transfection. In another aspect the invention is directed to a host cell transfected to produce useful amounts of a desired heterologous protein by transient expression. Yet another aspect of this invention is a transient expression system which optimizes the interaction between specific vector components and certain trans-activating proteins. Still another object is to increase expression in a transient system by transfection with translational control effectors.

BRIEF DESCRIPTION OF THE DRAWINGS

FIG. 10 Sequence of a portion of pF8CIS. The DNA sequence of the expression vector containing the cytomegalovirus enhancer, promoter (nucleotides 1-732), stabilizing sequence, i.e. splice donor intron sequence, the Ig variable region intron and splice acceptor sequence (nucleotides 733-900).

FIG. 11 Sequence of a portion of pF8SCIS. The DNA sequence of the expression vector containing the SV40 enhancer and promoter, (nucleotides 1-360) stabilizing sequence which includes cytomegalovirus donor and intron sequence, the Ig variable region intron and splice acceptor sequence (nucleotides 361-580).

FIG. 12 Sequence of a portion of pF8CSSS. The DNA sequence of the expression vector containing the cytomegalovirus enhancer promoter and leader (nucleotides 1-732), stabilizing sequence including the engineered splice donor and acceptor sequence (nucleotides 733-736), the remaining leader.

DETAILED DESCRIPTION

Definitions and General Methods

Figure 1A:
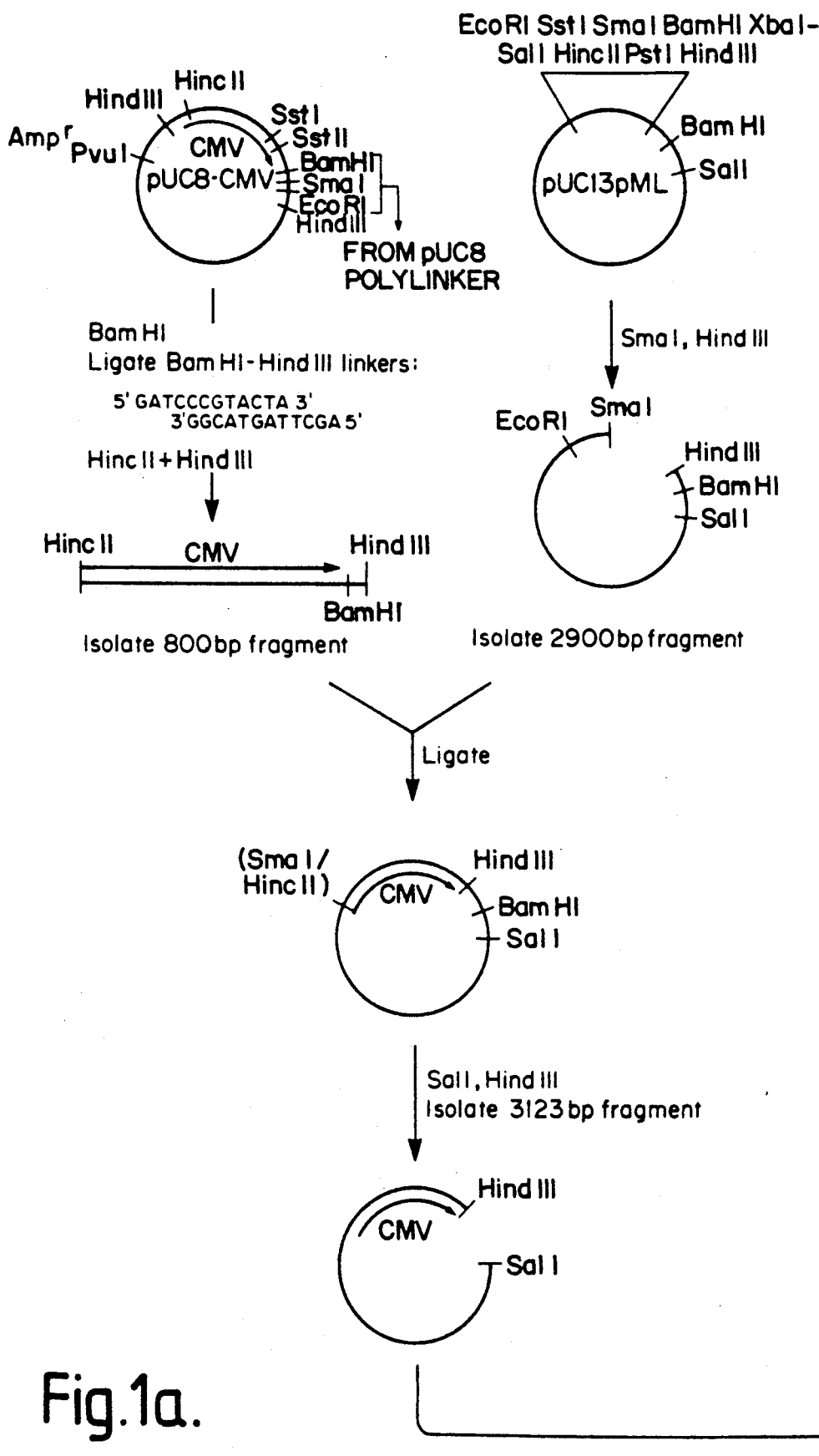
FIG. 1 Construction of a factor VIII expression vector used to establish production cell lines for factor VIII. pF8CIS.

As used herein, "nucleotide sequence" refers to a nucleic acid comprising a series of nucleotides in a 5' to 3' phosphate diester linkage which may be either an RNA or a DNA sequence. If a DNA, the nucleotide sequence may be either single or double stranded. Similarly, "DNA sequence" refers to both single and double stranded embodiments.

"Desired heterologous protein" refers to a protein which is desired to be expressed in a host cell, but which the host cell either normally does not produce itself or produces in small amounts, and which is not normally necessary for the cells continued existence. Such a protein includes any molecule having the pre or mature amino acid sequence and amino acid or glycosylation variants (including natural alleles) capable of exhibiting a biological activity in common with said desired heterologous protein. Examples of such proteins are: growth hormone, insulin, factor VIII, tissue plasminogen activator, tumor necrosis factor alpha and beta, lymphotoxin, enkephalinase, human serum albumin, mullerian inhibiting substance, relaxin, tissue factor protein, inhibin, erythropoietin, interferon alpha, beta and gamma, superoxide dismutase, decay accelerating factor, viral antigen such as, for example, a portion of the AIDS envelope, and interleukin.

"Splicing" refers to the mechanism by which a single functional RNA molecule is produced by the removal of one or more internal stretches of RNA during the processing of the primary transcript. Splicing is believed to begin with the looping out of the intron so that the 5' end of the intron (referred to as the donor) is juxtaposed to the 3'0 end of the intron (referred to as the acceptor). A comparison of the base sequences at intron-exon junctions reveals consensus sequences, with the first two bases at the 5' end of each intron being GT and the last two bases at the 3' end being AG.

"Spliced mRNA" refers herein to mRNA produced by either the removal of one or more internal stretches of RNA or by constructing a DNA which when transcribed produces a mRNA having the same properties as a mRNA which had been subject to splicing but from which no nucleotide sequence had in fact been removed.

"Stabilizing sequence" refers to a DNA sequence that gives rise to a spliced mRNA by coding either a splice donor-intron-acceptor sequence or by coding a sequence comprising a full consensus sequence or a part thereof for the donor and acceptor sequence and the appropriate nucleotides at the donor/acceptor junction such that the resulting mRNA resembles functionally a mRNA which had been spliced. The stabilizing sequence is placed in the leader sequence of the gene encoding the desired heterologous protein. "Leader sequence" refers to that region of mRNA that is in the 5' untranslated region between the CAP site and the AUG translation start signal.

"Consensus sequence" refers herein to the sequences

found to occur at the exon-intron boundary (or donor sequence) and

found to occur at the intron-exon boundary (or acceptor sequence). See Mount, S. M., Nucleic Acids Research 10(2), 459–472 (1982). Analyses of the frequency with which individual bases occur in particular positions yielded a consensus sequence for the donor and acceptor sequences. It is also known that introns begin with GT and end with AG. Breathnach, R. et al., PNAS (USA) 75 4853–4857 (1978). It is also known that certain multipartite leader sequences in which multiple splicing events occur may require additional factors of early gene function to achieve proper processing. See Babiss, L. E. et al., Mol. and Cell. Biol. 5(10), 2552–2558 (1985). One of ordinary skill in the art using the knowledge of the donor and acceptor consensus sequences, multipartite leader sequences in which multiple splicing events occur requiring early gene function and the consensus splice sequences rule in accord with the instant invention will be able to select a particular stabilizing sequence for a desired protein.

"Control region" refers to specific sequences at the 5' and 3' ends of eukaryotic genes which may be involved in the control of either transcription or translation. Virtually all eukaryotic genes have an AT-rich region located approximately 25 to 30 bases upstream from the site where transcription is initiated. Another sequence found 70 to 80 bases upstream from the start of transcription is a CXCAAT region where X may be any nucleotide. At the 3' end of most eukaryotic genes is an AATAAA sequence which may be the signal for addition of the polyadenylation tail to the 3' end of the transcribed mRNA.

"Promoter" refers to the nucleotide segment recognized by RNA polymerase molecules that start RNA synthesis. Promoters controlling transcription from vectors in mammalian host cells may be obtained from various sources for example, the genomes of viruses such as: polyoma, Simian Virus 40 (SV40), adenovirus, retroviruses such as, for example, rous sarcoma virus (RSV), hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. Fiers et al., 1978, "Nature", 273: 113. The immediate early promoter of the human cytomegalovirus is conveniently obtained as a HindIII E restriction fragment. (Greenaway, P. J. et al., Gene 18, 355–360 [1982]). The RSV promoter and enhancer may be obtained as a HindIII-NdeI digest from pRSVCat restriction fragment. (Gorman, C. et al., PNAS 70, 6777 [1982]). Of course, promoters from the host cell or related species also are useful herein.

"Enhancer" refers to cis-acting elements of DNA, usually about from 10–300 bp, that act on a promoter to increase its transcription. Transcription of a DNA encoding a desired heterologous protein by higher eukaryotes is increased by inserting an enhancer sequence into the vector. Enhancers are relatively orientation and position independent having been found 5' (Laimins, L. et al., PNAS 78, 993 [1981]) and 3' (Lusky, M. L., et al., Mol. Cell Bio. 3, 1108 [1983]) to the transcription unit, within an intron (Banerji, J. L. et al., Cell 33, 729 [1983]) as well as within the coding sequence itself (Osborne, T. F., et al., Mol. Cell Bio. 4, 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding the desired heterologous protein. The 3' untranslated regions also include transcription termination sites.

Expression vectors may contain a selection gene, also termed a selectable marker. A selection gene encodes a protein, sometimes referred to as a secondary protein, necessary for the survival or growth of a host cell transformed with the vector. Examples of suitable selectable markers for mammalian cells are dihydrofolate reductase (DHFR), thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR$^-$ cells and mouse LTK$^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media. Therefore, direct selection of those cells requires cell growth in the absence of supplemental nutrients.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1, 327 (1982), mycophenolic acid, Mulligan, R. C. and Berg, P. Science 209, 1422 (1980) or hygromycin, Sugden, B. et al., Mol. Cell. Biol. 5:410–413(1985). The three examples given above employ bacterial genes under eukaryotic control to convey resistance to the appropriate drug neomycin (G418 or geneticin), xgpt (mycophenolic acid) or hygromycin, respectively. In the following experiments the selective agent of choice is most often G418 geneticin unless specifically referring to CHO DHFR$^-$ cells. In this case the direct selection for DHFR production was used.

"Amplification" refers to the increase or replication of an isolated region within a cell's chromosomal DNA. Amplification is achieved using a selection agent e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater MTX to the media. Amplification of a desired gene can be achieved by cotransfecting a mammalian host cell with a plasmid having a DNA encoding a desired protein and the DHFR or amplification gene so that cointegration can occur. One ensures that the cell requires more DHFR, which requirement is met by replication of the selection gene, by selecting only for cells that can grow in successive rounds of ever greater MTX concentration. So long as the gene encoding a desired heterologous protein has cointegrated with the amplifiable gene, replication of this gene gives rise to replication of the gene encoding the desired protein. The result is that increased copies of the gene, i.e. an amplified gene, encoding the desired heterologous protein express more of the desired heterologous protein.

Preferred suitable host cells for expressing the desired heterologous proteins in higher eukaryotes include any cell line making the trans-acting proteins Ela and Elb such as human embryonic kidney line (293, Graham, F. L. et al. J. Gen Virol. 36, 59 [1977]; a clone of 293 cells adapted to grow in suspension in Joklicks media is referred to as 293s) and JW2 (Whittaker, J. L. et al., M. C .B. 4:110–116 [1984]). While these two cell lines have been transformed to produce endogenously the trans-activating proteins Ela and Elb, it is contemplated that other host cells may also be transformed with these or equivalent trans-acting proteins such that the host cell may be used in accord with the teaching of this invention. Such host cells include: baby hamster kidney cells (BHK, ATCC CCL 10); chinese hamster ovary-cells-DHFR (described by Urlaub and Chasin, PNAS (USA) 77 4216, [1980]); mouse sertoli cells (TM4, Mather, J. P., Biol. Reprod. 23, 243–251 [1980]); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); rat hepatoma cells (HTC, Ml.54, Baumann, H. et al., J. Cell Biol. 85, 1–8 [1980]); TRI cells (Mather, J. P. et al., Annals N.Y. Acad. Sci. 383, 44–68 [1982]); and, human KB cells (Babiss, L. E. et al., J. Virol 46:454–465 [1983]). Host cells were cultured in F12: DMEM (Cibco) 50:50 with added glutamine and without antibiotics.

"Trans-activating factors" refer to early viral proteins such as, for example, simian virus or (SV40) T antigen (Loeken, M. R. et al., M. C. B. 6:2020 [1986]; Robbins, P. D. et al., M. C. B. 6:1283 [1986]; Keller, J. M. and Alwine, J., M. C. B. 5:1859 [1985]), adenovirus Ela and Elb protein (Loeken M. R. [1986]Ibid; Triesmar, R., [1983]Supra; Gaynor, R. B. et al., PNAS 81:1193 [1984]; Imperiale, M. J. et al., Supra.) and the herpesvirus immediate early (IE) proteins (Everett, R. D. EMBO J. 3:3135 [1984]; Persson, R. H. et al., J. Virol. 54:414 [1985]); fos (Setoyama, C. et al., PNAS 83:3213 [1986]) and human and simian immunodeficiency virus (tat, virally encoded trans-activators) (Rosen, C. et al., Nature 319, 555-559 [1986]). These proteins are the products of genes containing efficient promoters. The transcriptional activation function of each trans-activating factor is to increase expression of other viral genes. These trans-activating factors may also activate promoters that are not homologous to their viral genes. While the aforementioned trans-activating factors are presently known, other trans-activating factors from other viral systems are contemplated.

"Translational control effectors" refers to certain RNA such as, for example, virus-associated RNA which effect translation of RNA encoding a desired heterologous protein. There are similar RNA polymerase III (pol III) transcripts present in Epstein Barr virus (EBV) (Bhat, R. A. and Thimmappaya, B., J. Virol 56, 750 [1985]) and HBV (AuFiero, B. et al., Abstract Conference on SV40 Polyma and Adenovirus [Cambridge, England, July, 1987] at p. 88) which may have similar translational control effects (Thimmappaya, B. et al., Cell 31:543 [1982]; Svenson, C. & Akusjarvi, G., EMBO J. 4:957 [1985]; Svenson, C. and Akusjarvi, G., EMBO J. 4:957 [1985]; Schneider, R. et al., Cell 37:291 [1984]). The suggested mechanism of action of such RNA has been described. (Reichel, P. A. et al., Nature 313:196 [1985]; Kitajewski, J. et al., Cell 45:195 [1986]; and, O'Malley, R. et al., Cell 44:391 [1986].

"Transformation" means introducing DNA into an organism so that the DNA is replicable, either as an extrachromosomal element or by chromosomal integration. Unless otherwise provided, the method used herein for transformation of the host cells is the method of Graham, F. and van der Eb, A., Virology 52, 456-457 (1973).

Host cells may be transformed with the expression vectors of the instant invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

"Transfection" refers to the taking up of an expression vector by a host cell whether or not any coding sequences are in fact expressed. Numerous methods of transfection are known to the ordinarily skilled artisan, for example, CaPO4 and electroporation. Successful transfection is generally recognized when any indication of the operation of this vector occurs within the host cell. However, in the context of the present invention successful transfection refers to stable continuous expression of a desired heterologous protein by a host culture over numerous generations.

"Transient expression" refers to unamplified expression using the method of the instant invention within about one day to two weeks of transfection. The optimal time for transient expression of a particular desired heterologous protein may vary depending on several factors including, for example, the particular desired heterologous protein, the transacting protein, the translational control effector and the host cell. Transient expression occurs when the particular plasmid that has been transfected functions, i.e., is transcribed and translated to produce the desired protein. During this time the plasmid DNA which has entered the cell is transferred to the nucleus. The DNA is in a nonintegrated state, free within the nucleus. Transcription of the plasmid taken up by the cell occurs during this period. Vectors which were identified as capable of producing the desired heterologous protein transiently may then be used to establish a stable continuous production cell. Transient expression refers to a short period following transfection that is about one day to about two weeks, preferably one day to about seven days and most preferably from about one day to about four days, although this may vary depending on the factors discussed above. Following transfection the plasmid DNA may become degraded or diluted by cell division. Random integration within the cell chromatin occurs. Transient expression in accord with the invention produces transformed cells with stable transfected DNA capable of producing usable amounts of a desired protein.

An assay based on immunoperoxidase staining of a transfected cell was developed to assess quickly whether a desired heterologous protein had been expressed. (Gorman, C. M. et al., Cell 42, 519-522 [1985]). Monoclonal antibodies specific for the desired heterologous protein were screened for use in this assay. Host cells containing the vector were stained and compared to parental cell line for screening cells which produce a specific protein. A monoclonal antibody was selected which gave the strongest signal with the least amount of background. Transient transfections were performed to test vectors for the ability to produce a desired protein. Cells (Cos, 293, CHO, BHK, TM4) were transfected using the CaPO4 technique. (Graham and van der Eb modified by Gorman, C. M. et al., Science 221, 551-553 (1983)). We used ten micrograms per milliliter of precipitate of the specific protein vector to be tested. The precipitates were left on the cells for 3-4 hours. Cells were then glycerol shocked for an average of one minute. Thirty-six hours after transfection cells were fixed with acetone-methanol (50:50) and washed with phosphate buffer saline (PBS). Staining was performed using either a monoclonal antibody supernatant undiluted or purified antibody diluted 1:3000 in PBS containing 10% fetal calf serum. This first antibody remained on the cells for 2 hours. Plates were placed on a slow shaker during this time. Cells were washed 5 times over a ten minute period. The second antibody used was rabbit anti-mouse IgG (Dakopatts). This was diluted in PBS+fetal calf serum at a dilution of 1:150. A two hour incubation was followed by another series of washes. To develop the peroxidase reagent ortho-diansidine was used as a substrate. An ethanol saturated solution of ortho-diansidine was diluted 1:100 in PBS with 1:10,000 dilution of hydrogen peroxide. This substrate was left on the cells for 2 hrs at room temperature or overnight at 4° C.

By this method a wide variety of vectors encoding the desired protein were quickly screened for the ability to direct protein expression.

In order to simplify the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences, restriction sites, in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 10 μg of DNA would be digested with 20 to 40 units of enzyme in a larger volume. Appropriate buffers and substrate amounts for particular restriction enzymes are specified by the manufacturer. Incubation times of about one hour at 37° C. are ordinarily used, but may vary in accordance with the supplier's instructions. After digestion the reaction was run directly on a gel to isolate the desired fragment.

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional. Maniatis, T. et al., 1982, *Molecular Cloning* pp. 133-134. Reactions using BAP are carried out in 50 mM Tris at 68° C. to suppress the activity of any exonucleases which may be present in the enzyme preparations. Reactions were run for one hour. Following the reaction the DNA fragment is gel purified.

"Oligonucleotides" refers to short length single or double stranded polydeoxynucleotides which are chemically synthesized by known methods and then purified on polyacrylamide gels.

"Ligation" refers to the process of forming phosphodiester bonds between two double stranded nucleic acid fragments (Maniatis, T. et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2-15 μg of the target DNA in 10 mM MgCl$_2$, 1 mM dithiothreitol, 50 mM NaCl, 10 mM Tris (pH 7.5) buffer at about 37° C. in the presence of 8 units of the Klenow fragment of DNA polymerase I and 250 μM of each of the four deoxynucleoside triphosphates. The incubation generally is terminated after 30 min. phenol and chloroform extraction and ethanol precipitation.

"Northern" blotting is a method by which the presence of a cellular mRNA is confirmed by hybridization to a known, labelled oligonucleotide or DNA fragment. For the purposes herein, unless otherwise provided, Northern analysis shall mean electrophoretic separation of the mRNA on 1 percent agarose in the presence of a denaturant (formaldehyde 7%), transfer to nitrocellulose hybridization to the labelled fragment as described by Maniatis, T. et al., Id., p. 202.

The following examples merely illustrate the best mode now known for practicing the invention, but should not be construed to limit the invention. All literature citations herein are expressly incorporated by reference.

EXAMPLE 1

General Methods for a Transient Expression System a) Chloramphenicol acetyltransferase (CAT) encoding plasmids.

The entire region containing the CMV enhancer promoter and splice donor region (described in Example 3, subparagraph 1[a][1]) below was cloned into pUC8 (New England Biolabs). The CMV promoter was removed from the pUC8 construct by HpaII blunt-BamHI linker and HindIII digest which was cloned into pUC19 (New England Biolabs) (referred to as pUC.CMV) to increase the available cloning sites and to remove the splice donor sequence located 120 bp 3' of the cap site. The CAT coding region, including the t splice of SV40 T antigen and the poly adenylation site was subcloned from pSV2CAT (Gorman, C. et al., Mol. Cell. Biol. supra) as a HindIII-BamHI fragment and inserted into the pUC.CMV vector to yield pUC.CMVCAT. pCMVpro, a vector which has the majority of the CMV enhancer removed, was constructed by cutting pUC.CMVCAT with AatII. This 3' overhang was filled in with polI and the vector was cut with BamHI. This fragment was subcloned into pUC18 (New England Biolabs) at the SmaI and BamHI sites. This vector contains 100 bp upstream of the CMV TATA box region so that the CAAT box and GC rich region are also conserved. For comparison, vectors containing the SV40 enhancer and promoter (pSV2cat) (Gorman, C. et al., Mol. Cell. Biol. supra) or the SV40 promoter alone (pSV1cat) (Gorman. C. et al. Ibid) were also used. Two additional vectors containing the CMV enhancer and the SV40 promoter (pCMVSVcat construction described below), and one containing the SV40 enhancer and the CMV promoter (pSVCMVcat construction described below) were constructed. An internal control plasmid used during CAT transfection experiments comprised the DNA encoding hGH (via an EcoRI fragment cloned into pUC8; see U.S. Pat. No. 4,342,832) cloned 3' of the RSV LTR. The poly A addition site of the hepatitis surface antigen was used in this vector, pRSVhGH.

To construct pSVCMVcat, which contains the SV40 enhancer and the CMV promoter we started with the pCMVpro vector described above. The unique KpnI site of pUC18 was cut and the 3' overhang was blunted as described by DNA polymerase I. Into this blunt site which is immediately 5' to the CMV promoter, we inserted the SV40 enhancer. We obtained this enhancer as a 234 bp NcoI-PvuII fragment from pSV2cat. After the 5' overhang of the NcoI end was blunted by a Klenow reaction a blunt end ligation resulted in the vector pSVCMVcat.

To construct the plasmid containing the CMV enhancer and the SV40 promoter, pSV2cat (Gorman, C. et al., 1982 supra) was digested with SphI and AccI. The resulting 3' overhanging ends were blunted using the exonuclease activity present in the holoenzyme of DNA polymerase I. A 482 bp piece of the DNA, containing the CMV enhancer, was inserted into this region, just 5' to the SV40 promoter. To obtain this 482 bp piece, pUC.CMV was digest with BanI and HindIII. Following a Klenow reaction to blunt the BamI site, the fragment was ligated to the fragment from pSU2cat to yield pCMVSVcat.

For high levels of transient expression in 293 cells a series of CMV driven hGH vectors were constructed. The prototype vector pF8CIS, described below in Example 3, was modified by placing the factor VIII cDNA with a poly-linker encoding for the restriction enzyme recognition sites for ClaI, XbaI, XhoI, NotI and HpaI. The DNA for hGH was subcloned as a blunted EcoRI fragment into a blunted XhoI site. The first vector in this series, pCIShGH, contains the SV40 poly A addition site 3' of the hGH cDNA followed by an SV40-mouse dyhydrofolate reductase (DHFR) transcription unit. pCIS4hGH has the entire SV40 early promoter-origin-DHFR region removed so that this vector no longer can replicate in mammalian cells in the presence of SV40 T antigen. pCIS5hGH has the SV40 origin remaining but the cDNA for DHFR and the hepatitis surface antigen poly A addition site removed. Expression was increased by removal of the DHFR gene while maintaining the SV40 origin allowing for replication.

b) Adenoviral gene vectors

The ElA DNA (Zerler, B. et al., M. C. B. 7:821 [1987]) was subcloned from adenovirus DNA into pUC8 to give pUC.ElA. The plasmids contained the cDNA for the 12S and 13S messages of Ela. The plasmid containing the Elb DNA is described by Ruley, H. E. Nature 304:602 [1983]. pUC.VA was made by subcloning a SmaI-HindIII fragment of adenovirus containing the VA RNA genes (available commercially from New England Biolabs) into pUC19.

SV40 T antigen, as described in Rio, D. C. et al., Science 227:23 [1985], was used for replication studies. The plasmid was labelled by pRSVT$^s$.

c) Transfection

CaPO4 method was used for transfection. CAT transfections used a total of 5 micrograms of DNA for 0.5 ml of precipitate for transfection of 60 mm dishes. Of this 5 micrograms, 0.5 to 1 microgram was CAT encoding DNA, 100 nanograms was pRSVhGH and the remaining DNA was carrier composed of pUC plasmid. At 36 hours following transfection, supernatants were assayed for hGH levels by the ImmunoRadioMetric Assay (IRMA) assay (commercially available from Hybritech) and cells were harvested for preparation of cell lysates for the CAT assay. Cat activity was assayed by use of $C^{14}$ chloramphenicol (CM) as described by Gorman et al., or by the method using $H^3$ sodium acetate (de Crombrugghe, et al., Nature 241:237 [1973]) modified by Nordeen, S. K. et al., DNA 6:173 (1987). CAT activity was standardized for differences in transfection efficiency according to the basal level of hGH assayed in each sample.

Transient production of hGH in 100 mm dishes by transfection with 1 ml of precipitate containing 10 micrograms of hGH plasmids and 105 micrograms of pUC.VA DNA. A time course of expression was determined by assaying supernatants from 4 to 72 hours following glycerol shock. These supernatants were assayed by IRMA.

EXAMPLE 2

Effect of Trans-Activating Factor on Expression

Expression of the SV40 enhancer-promoter region in 293 cells appears to be enhancer independent. No additional effect on RNA synthesis is seen by the inclusion of the SV40 enhancer. Trans-activating factors which bind, and appear to repress both the SV40 and polyoma immunoglobin enhancer are present in cells containing Ela (Borelli, E. et al., Nature 312:608 [1984]; Velcich, A. and Ziff, E., Cell 40:705 [1985]; Hen, R. et al., Science 230:1391 [1985]; Hen, R. et al., Nature 321:249 [1986]). Transcription from the Rous sarcoma virus (RSV) long terminal repeat (LTR) is also repressed in 293 and JW2 cells or in the presence of Ela. The RSV LTR is known to direct initiation of RNA synthesis very efficiently in primate cells (Gorman, C. et al., PNAS 79:6777 [1982]; Gorman, C. et al., Science 221:551 [1983]). But, as seen in Table 1, the relative level of CAT expression is much less from the RSV promoter in 293 and JW2 cells when compared to expression in other primate lines. In cotransfection experiments with pRSVhGH conducted in CV1 cells with and without Ela, the hGH levels decreased by 20 fold in the presence of Ela. The average level of hGH assayed in CV-1 cells transfected with 100 ng of pRSVhGH is 58 ng/ml. When 1 microgram of Ela containing plasmid is included in these transfections this level drops to 3 ng/ml.

TABLE 1

Analysis of Species Preference of the CMV Promoter

| Enhancer | Promoter | Cell Type | | | | | |
|---|---|---|---|---|---|---|---|
| | | CHO | CV1 | 293 | Hela | BHK | JW2 |
| CMV | CMV | 100 | 100 | 100 | 100 | 100 | 100 |
| SV40 | SV40 | 67 | 87 | 20 | 5 | 60 | 26 |
| CMV | SV40 | 130 | 87 | 40 | 18 | 120 | 48 |
| SV40 | CMV | 40 | 83 | 85 | 25 | 15 | 108 |
| RSV | RSV | 76 | 66 | 46 | 73 | 60 | 32 |

The CMV enhancer has been shown to be a strong enhancer in a wide variety of cell types (Boshart et al., 1985 Supra). Surprisingly we have seen that the CMV promoter does exhibit a strong species specificity being particularly weak in hamster cells and very strong in primate lines, particularly in human cells (Table 1). With the SV40 enhancer present, as in lines 2 and 4, the SV40 promoter is four fold more efficient in the hamster cell lines than is the CMV promoter. This is confirmed by the data in lines 1 and 3 of Table 1. The CMV promoter is efficient in all three human cell lines shown i.e. 293, Hela and JW2. The absolute amount of CAT activity differs between cell types. Expression is greater in 293 cells than in CV1, CHO or BHK cells. This large amount of CAT protein is not simply due to differences in transfection efficiencies since CHO, CV1 and 293 cells were all transfected with relatively the same efficiency.

The effect of trans-activating factors of the early adenoviral genes on the expression of the CMV enhancer and promoter was studied. No consistent repression of the CMV enhancer-promoter unit as seen with SV40, polyoma or RSV was observed (Table 2). However, it was observed that the CMV promoter is trans-activated by cotransfection with Ela. This increased expression an average of 12 fold.

TABLE 2

| Effect of Ela on the Enhancer and Promoter | | | | | |
|---|---|---|---|---|---|
| Experiment | | | | +Ela | |
| Enhancer | Promoter | 1 | 2 | 1 | 2 |
| SV40 | SV40 | 70 | 72 | 3 | 2 (29<) |
| CMV | SV40 | 70 | 65 | 90 | 86 (1.3>) |
| SV40 | CMV | 50 | 66 | 40 | 45 (1.5<) |
| CMV | CMV | 100 | 100 | 155 | 137 (1.4>) |
|  | CMV | 23 | 12 | 370 | 124 (13>) |

The Ela region codes for five (5) separate messages, i.e. proteins. (Perricoudet, M. G. et al., Nature 281, 694[1929]; Ulfendall, P. J. et al., [1987]supra at 130; Stephens, C. and Harlow, E., Abstract, Polyoma and Adenovirus Conference [Cambridge, England, 1987]). The proteins encoded by two of these messages were studied for their transcriptional activation effects. The effect of the entire Ela region and the separate effects of the 12S and 13S encoded proteins were studied. CV1 monkey kidney cells were cotransfected with a variety of CAT encoding plasmids and plasmids containing the entire Ela region of the cDNA's for the 12S or 13S message. (Roberts, B. E. et al., J. Virol. 56, 406[1985]). A small amount of an internal control plasmid containing the hGH gene was included as described. Cotransfection of CV1 cells with plasmids encoding the 12S and 13S messages of Ela separately resulted in the 12S encoding protein having little effect on expression where the CMV enhancer is present. This message has been shown to repress some enhancers. Table 3 shows that cotransfection of the 13S cDNA has a strong positive effect on CMV directed transcription by increasing CAT activity 7-15 fold. The largest increase in expression is seen with the enhancer minus construct, was a 15 fold increase on the promoter alone. When the entire Ela region is included in the transfection there is a marginal effect on the enhancer + promoter combination of CMV. However, under these conditions there is a 16 fold increase on the promoter alone.

TABLE 3

Analysis of the Effect of Specific Ela Proteins on the CMV Enhancer and Promoter A. CV1 cells cotransfected with:

|  | Enhancer + Promoter | Promoter |
|---|---|---|
| pUC19 | 100 | 21 |
| 12S | 118(1) | 33(1.5) |
| 13S | 694(7) | 312(14) |
| entire Ela | 123(1.2) | 345(16) |

Experiments on trans-activation in 293 cells has focused on the role of Ela. However, these cells are known to also express Elb proteins. (Graham, F. et al., supra 1977). In an attempt to address what role the Elb proteins may have on expression we conducted experiments with cotransfection of an Elb expressing plasmid. In these experiments we again used CV1 cells and assayed for CAT activity following transfection of either the CAT plasmids alone, CAT plasmids cotransfected with Elb, or finally, the CAT plasmids cotransfected with both Ela and Elb. As seen in Table 4, cotransfection with Elb alone increases the CAT levels 4-10 fold. The largest increase was again seen with the pCMVpro construction which uses the CMV promoter, without enhancer to direct CAT expression. And in contrast to the above results where Ela alone had a negative effect on some vectors (Table 2), coexpressing Ela and Elb had a positive effect on all vectors (Table 4). A striking additive effect is seen with the vectors which use the CMV promoter directed expression increasing from 6 to as high as 30 fold.

TABLE 4

| Effect of Elb Region on CAT Expression | | | | |
|---|---|---|---|---|
| Enhancer | Promoter | Alone | Elb | Ela + Elb |
| SV40 | SV40 | 70 | 416(6) | 273(4) |
| CMV | SV40 | 67 | 254(4) | 200(3) |
| SV40 | CMV | 50 | 543(11) | 339(7) |
| CMV | CMV | 100 | 385(4) | 594(6) |
|  | CMV | 23 | 267(11) | 489(20) |

Analysis of Plasmid Stability

Few reports have attributed a role in transcriptional activation to Elb alone. Additionally, however, the Elb proteins, specifically the 19K protein, has been shown to effect the stability of both host cell and viral DNA. (White. E. et al. 1986, MCB 6:3763; Pilder, S. J. et al. 1984, J. Virol. 52:664; Subramanian, T. et al. 1984, J. Virol. 52:336; Takemori, N. et al. 1984. J. Virol. 52:793). This process is little understood and is complex requiring coexpression of Ela proteins for this effect to be detected. We have thus asked whether plasmid DNA is also more resistant to degradation in the presence of either or both of these early adenovirus genes.

Following transfection of pRSVhGH DNA into two cell lines containing Ela and Elb and into cells lacking these genes such as CV1, Cos7, Hela or KB cells, cells were harvested at various times from 4 hours to 80 hours for isolation of plasmid DNA by the Hirt method. (Hirt, B. I. Mol. Biol. 26, 365[1967]). DNA remaining on the outer surface of the cells was removed by treatment with DNase. The presence of pRSVhGH DNA at varying times post transfection was determined by Southern blot with an hGH specific probe. The two monkey kidney cell lines, CV1 and its derivative Cos7, had plasmid DNA detectable by the Hirt method for 24 hours. Interestingly, the expression of T antigen in Cos7 cells had no effect on the maintenance of this plasmid DNA in absence of replication. The plasmid DNA was stable for 4 hours in Hela cells. Plasmid DNA was detected for up to 72 hours in the 293, 293s and JW2 cells. All of these cells express both the Ela and Elb regions of adenovirus. Since their morphological phenotype is very different, the adenoviral proteins present in these cells may be responsible for the increased stability of episomal DNA in these cell lines.

EXAMPLE 3

Expression Vector Factor VIII

1. Construction of Expression Vectors

The cDNA encoding human factor VIII was used in the construction of plasmids which would direct the expression of factor VIII protein in transfected mammalian cells (Wood, W. et al., Nature [Lond.] 312:330-337 [1984]). Those transformed mammalian cells secreted approximately 0.14 mU/ml of factor VIII. The instant method provides continuous production of factor VIII with yields significantly greater.

a) pF8CIS

The vector pF8CIS containing the cytomegalovirus enhancer (Boshart, M. et al, Cell 41, 520 [1985]) and promoter (Thomsen, D. R. et al., PNAS 81, 659-663 [1984]), the cytomegalovirus splice donor site and a portion of an intron (Sternberg, R. M. et al. T. of Virol.49, 190-199 [1984]), the Ig variable region intron and splice acceptor site, the cDNA encoding factor VIII and the SV40 polyadenylation site was constructed.

Figure 1B:
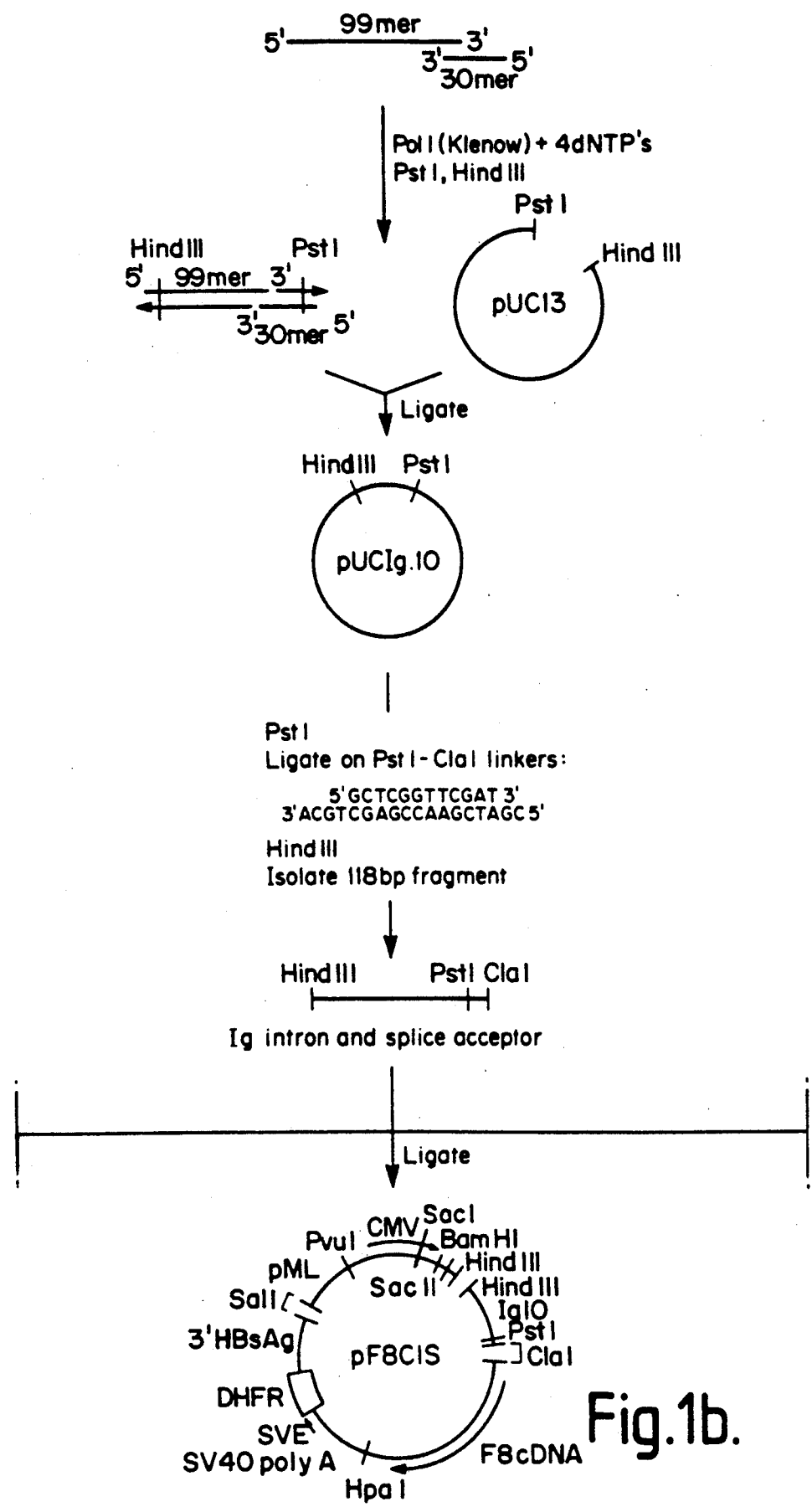
Figure 1C:
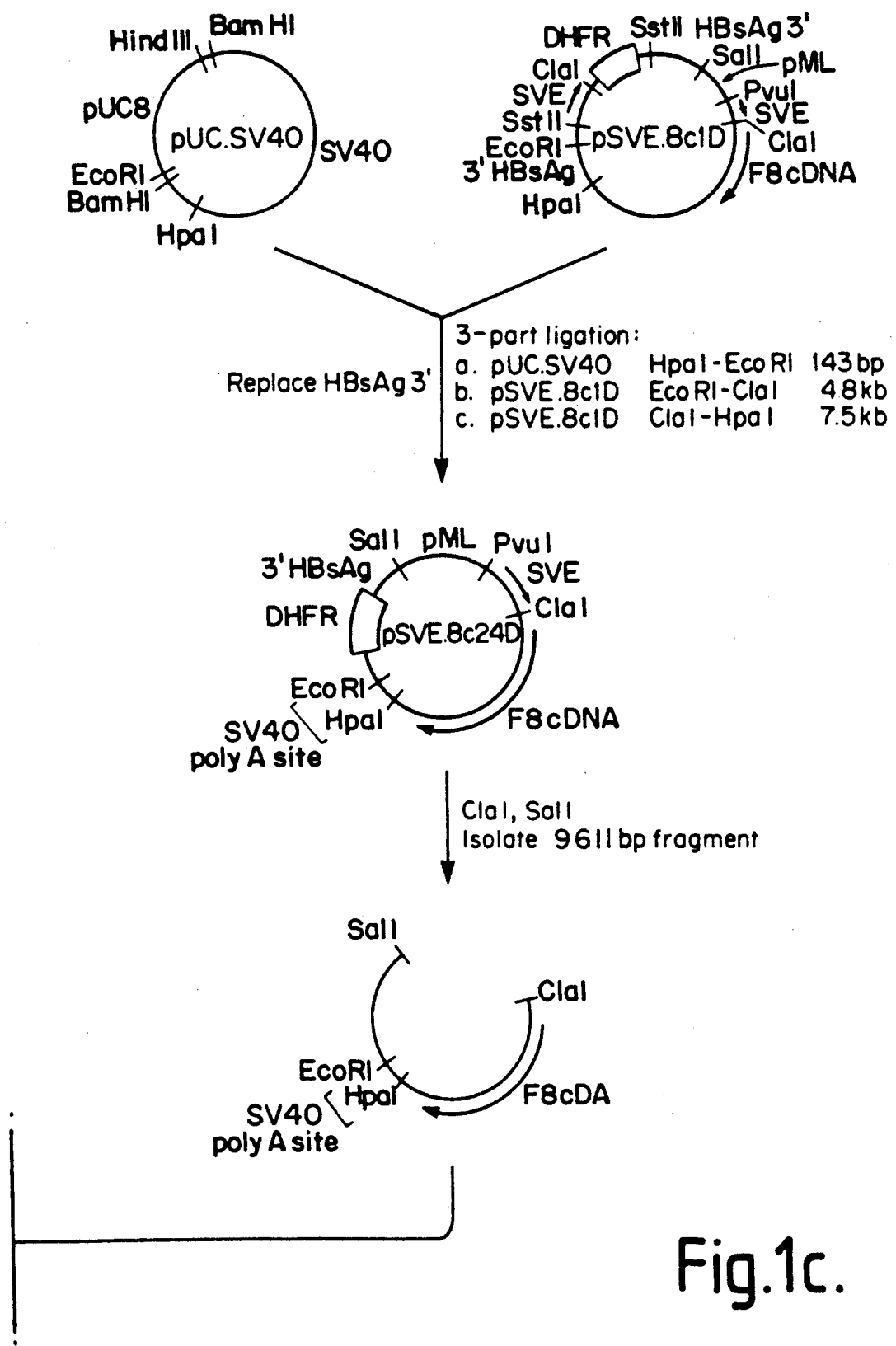

FIG. 1 shows the steps for construction of the factor VIII expression vector used to establish production cell lines for factor VIII. The three parts of the construction are detailed below.

1) The ampicillin resistance marker and replication origin of the final vector was derived from the starting plasmid pUC13pML a variant of the plasmid pML (Lusky, M. and Botchen, M., Nature 293, 79 [1981]). pUC13pML was constructed by transferring the polylinker of pUC13 (Veira, J. and Messing, J., Gene 19:259(1982)) to the EcoRI and HindIII sites of pML. A second starting plasmid pUC8CMV was the source of the CMV enhancer, promoter and splice donor sequence. pUC8CMV was constructed by inserting nucleotides 1 through 732, shown in FIG. 17, for the CMV enhancer, promoter and splice donor sequence into the blunted PstI and SphI sites of pUC8. Veira, J. and Messing, J. supra. Synthetic BamHI-HindIII linkers (commercially available from New England Biolabs) were ligated to the cohesive BamHI end creating a HindIII site. Following this ligation a HindIII-HincII digest was performed. This digest yielded a fragment of approximately 800 bp which contained the CMV enhancer, promoter and splice donor site. Following gel isolation this 800 bp fragment was ligated to a 2900 bp piece of pUC13pML. The fragment required for the construction of pF8CIS was obtained by digestion of the above intermediate plasmid with SalI and HindIII. This 3123 bp piece contained the resistance marker for ampicillin, the origin of replication from pUC13pML and the control sequences for the CMV including the enhancer, promoter and splice donor site.

2) The Ig variable region intron and splice acceptor sequence was constructed using a synthetic oligomer as shown in the central portion of FIG. 1. A 99 mer and a 30 mer were chemically synthesized having the following sequence for the IgG intron and splice acceptor site (Bothwell et al., 1981):

```
 1  5' AGTAGCAAGCTTGACGTGTGGCAGGCTTGA ...
31     GATCTGGCCATACACTTGAGTGACAATGA ...
60     CATCCACTTTGCCTTTCTCTCCACAGGT ...
88     GTCCACTCCAG3'

1  3' CAGGTGAGGGTGCAGCTTGACGTCGTCGGA5'
```

DNA polymerase I (Klenow fragment) filled in the synthetic piece and created a double stranded fragment. Wartell, R. M. and W. S. Reznikoff, Gene 9, 307 (1980). This was followed by a double digest of PstI and HindIII. This synthetic linker was cloned into pUC13 (Veira, J. and Messing, J., Gene 19, 259 [1982]) at the PstI and HindIII sites. The clone containing the synthetic oligonucleotide, labelled pUCIg.10, was digested with PstI. A ClaI site was added to this fragment by use of a PstI-ClaI linker. Following digestion with HindIII a 118 bp piece containing part of the Ig intron and the Ig variable region splice acceptor was gel isolated.

3) The third part of the construction scheme replaced the hepatitis surface antigen 3' end with the polyadenylation site and transcription termination site of the early region of SV40. A vector, pUC.SV40 containing the SV40 sequences was inserted into pUC8 at the BamHI site described in Viera, J. and Messing, J., supra. pUC.SV40 was then digested with EcoRI and HpaI. A 143 bp fragment containing only the SV40 polyadenylation site was gel isolated from this digest. Two additional fragments were gel isolated following digestion of pSVE.8clD. European Patent Publication No. 160,457. The 4.8 kb fragment generated by EcoRI and ClaI digest contains the SV40-DHFR transcription unit, the origin of replication of pML and the ampicillin resistance marker.

The 7.5 kb fragment produced following digestion with ClaI and HpaI contains the cDNA for factor VIII. A three-part ligation yields pSVE.8c24D. This intermediate plasmid was digested by ClaI and SalI to give a 9611 bp fragment containing the cDNA for factor VIII with an SV40 polyadenylation and transcription termination sites followed by the SV40 DHFR transcription unit.

The final three part ligation to yield pF8CIS used: a) the 3123 bp SalI HindIII fragment containing origin of replication, the ampicillin resistance marker and the CMV enhancer, promoter and splice donor; b) The 118 bp HindIII-ClaI fragment containing the Ig intron and splice acceptor; and, c) a 9611 bp ClaI-SalI fragment containing the cDNA for factor VIII, SV40 polyadenylation site and the SV40 DHFR transcription unit. A portion of the sequence of the expression vector pF8CIS is shown in FIG. 10.

b) pF8CSSS

The vector pF8CSSS containing the cytomegalovirus enhancer and promoter, an engineered stabilizing sequence, the cDNA encoding factor VIII and the SV40 polyadenylation site was constructed. The entire intron region including donor and acceptor sequences was deleted and replaced by an engineered stabilizing sequence. The stabilizing sequence is a synthetic double stranded oligomer having a sequence of the mature mRNA following splicing. The stabilizing sequence was inserted between the unique SacII-ClaI sites of pF8CIS. The sequences of the synthetic oligomers are as follows:

```
SacII
5'GGCCGGGAACGGTGATTGGAACGCG
3'CGCCGGCCCTTGCCACTAACCTTGCGC

5'GATTCCCCGTGCCAAGAGTGACGGTGT
 CTAAGGGGCACGGTTCTCACTGCCACA

5'CCACTCCCAC  GTCCAACTGC
 CGTGAGGGTG  CAGGTTGACG

5'AGCTCCGGTTCGAAT3'
 TCGAGGCCAAGCTTAGC5'
ClaI
```

The synthetic oligomers comprise the appropriate nucleotides of the donor and acceptor consensus splice sequences. The juxtaposition of the splice donor sequence to the splice acceptor sequence is indicated by the underline. This vector resembles the pF8CIS vector discussed above except for the deletion of the intron portion and replacement with an engineered stabilizing sequence. This construction eliminates the actual splicing of the noncoding region from recently the transcribed mRNA. A portion of the sequence of the expression vector pF8CSSS containing the engineered stabilizing sequence is shown in FIG. 12.

c) pF8SCIS

The vector pF8SCIS containing the SV40 enhancer and promoter, the cytomegalovirus splice donor site and a portion of the intron, the Ig intron and splice acceptor site, the cDNA encoding factor VIII and the SV40 polyadenylation and transcription termination sites was constructed.

Figure 2:
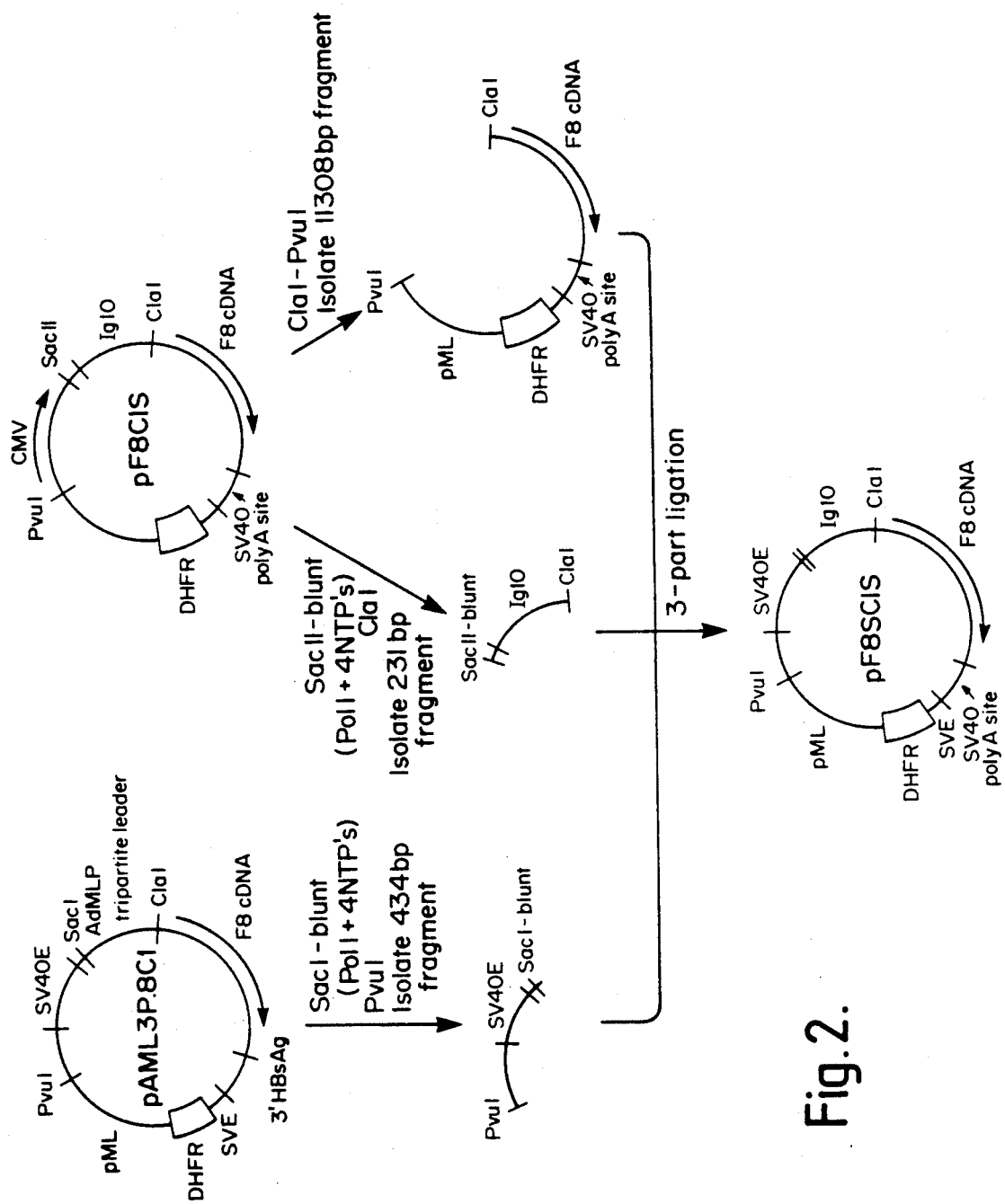
FIG. 2 Construction of a factor VIII expression vector used to establish production cell lines for factor VIII. pF8SCIS.

FIG. 2 shows the construction of pF8SCIS.

This vector was constructed using a three part ligation. The preparation of each of the three fragments of DNA used in this ligation is described below:

The first fragment contained the SV40 early region promoter and enhancer and one half the ampicillin resistance marker which was obtained from plasmid pML. The starting plasmid for the first of three fragments was pAML3P.8Cl. European Patent Publication No. 160,457. This plasmid was cut with SacI. Using the whole enzyme DNA polymerase I this 3' overhang created by SacI was blunted. Following this reaction the plasmid was cut with PvuI. The desired 434 bp fragment was isolated from an acrylamide gel.

The second and third fragments used in this construction were isolated from the plasmid pF8CIS which is described above.

Fragment 2 contained the splice donor from CMV immediate early gene and part of the following intron and the intron and splice acceptor synthetically made as described above. pF8CIS was cut with SacII and the resulting 3' overhang was blunted by the use of DNA polymerase I. This reaction was followed by cleavage with ClaI. Since the sequence surrounding the ClaI site in pF8CIS prevents cleavage if the plasmid is grown in a methylation plus strain, pF8CIS was prepared from dam⁻ strain GM48. Marinus, M. G. and Maris, N. R., Bacteriol. 114, 1143-1150 (1973) and Geier, G. E. and Madrid, P., J. Biol. Chem. 254, 1408-1413 (1979). Since both SacII and ClaI are unique sites in this vector the 231 bp fragment was easily isolated from an agarose gel.

The third fragment contains the cDNA for factor VIII, SV40 early region polyadenylation site, a SV40-DHFR transcriptional unit, the origin of replication of pML and half of the ampicillin gene. The 11308 bp fragment was prepared by digestion of pF8CIS (dam⁻) with ClaI and PvuI.

The three part ligation creating pF8SCIS destroys the SacI and SacII sites, maintains the ClaI site and reconstructs the amp$^r$ gene at the PvuI site. A portion of the nucleotide sequence of the expression vector pF8SCIS is shown in FIG. 11.

EXAMPLE 4

Transient Expression

Factor VIII expression was assayed based on immuno-peroxidase staining of transfected cells. Gorman et al. Cell 42, 519-526 (1985). This assay was used to test vectors for the expression of factor VIII. Twelve monoclonal antibodies specific for factor VIII were screened for use in this assay. BHK 31A3B cells (European Patent Publication No. 160,457) were stained and compared with parental BHK line to screen cells which produce factor VIII. Monoclonal antibody BH6 was found to give the strongest signal with the least amount of background. Transfections were performed and transient expression of factor VIII was assessed. Cells (Cos, 293, CHO, BHK, TM4) were transfected using the CaPO4 technique. Ten micrograms per milliliter of factor VIII vector precipitate was tested. The precipitates were left on the cells for 3-4 hours. Cells were then glycerol shocked for an average of 1 minute. Thirty-six hours after transfection cells were fixed with acetone-methanol (50:50) and washed with phosphate buffer saline (PBS). Cells were stained using either BH6 supernatant undiluted or purified BH6 antibody diluted 1:3000 in PBS containing 10% fetal calf serum. This first antibody remained on the cells for 2 hours. Plates were placed on a slow shaker during this time. Cells were washed 5 times over a ten minute period. A second antibody of rabbit anti-mouse IgG (Dakopatts) was diluted in PBS+fetal calf serum at a dilution of 1:150. A two hour incubation was followed by another series of washes. Ortho-diansidine (Sigma) was used as a substrate for developing the peroxidase reagent. A ethanol saturated solution of ortho-diansidine was diluted 1:100 in PBS with 1:10,000 dilution of hydrogen peroxide. This substrate was left on the cells for 2 hrs at room temperature or overnight at 4° C.

Figure 3A:
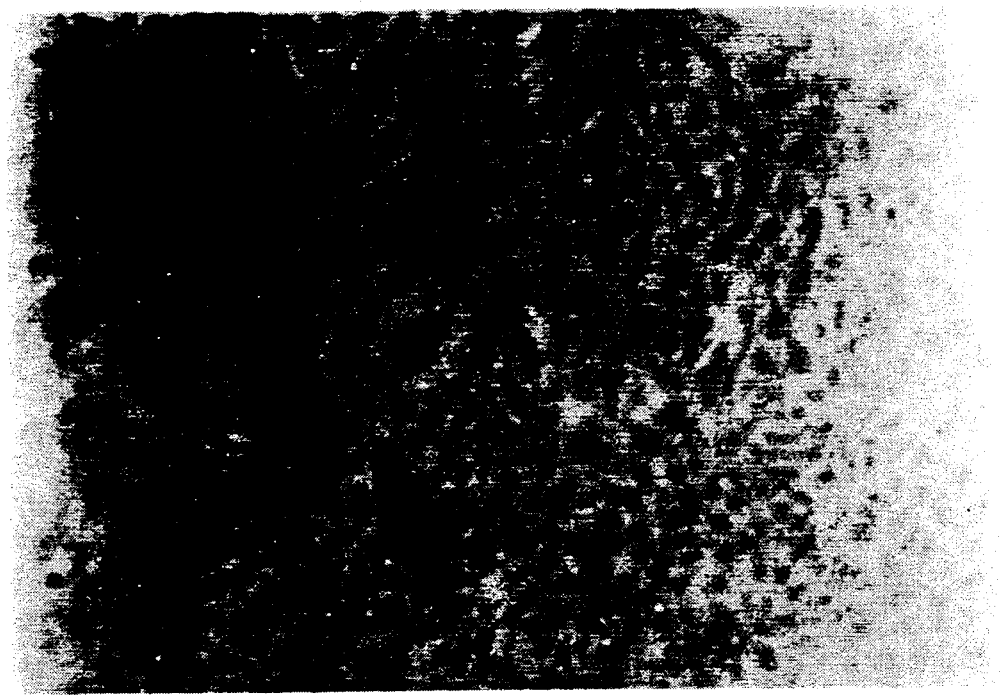
FIG. 3 Immunoperoxidase staining of cells following transfection (A) shows expression following transfection with pF8CIS (B) shows expression following transfection with pF8SCIS.
Figure 3B:
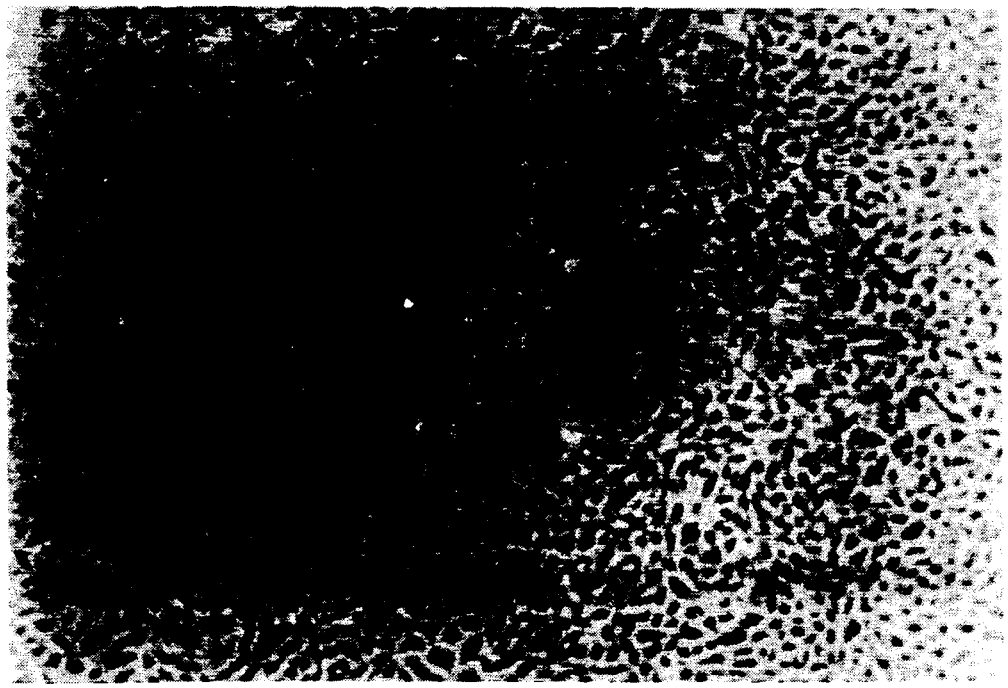

This method provided a screen for those factor VIII vectors directing factor VIII expression took place. This method indicated that transient factor VIII expression. Staining thirty-six hours after transfection provides an indication of whether the vector was transcribed and the mRNA translated.

pF8CIS directed transient expression of factor VIII in at least five different cell lines: COS, 293, CHO, TM4 and BHK. FIG. 3A shows transient expression of the vector pF8CIS in CHO cells.

pF8SCIS was found to direct transient expression of factor VIII as efficiently as pF8CIS. FIG. 3B shows transient expression of the vector pF8SCIS in CHO cells. Since the CMV enhancer and promoter can be completely replaced by the analogous SV40 enhancer and promoter, factor VIII production is not dependent on the specific transcriptional start signal but rather is dependent on other parts of the control region such as the stabilizing sequence site in the vector.

At the same time that cells were transfected to establish a production cell line, a dish of each cell type was assayed for transient expression. Results of the transient expression screen for factor VIII produced two classes of cells: those cell types which stained positively for factor VIII thirty-six hours after transfection (Category 1); and, those cell types having no detectable transient expression of factor VIII (Category 2). The host cells comprising each category are indicated below:

| Category 1 | Category 2 |
|---|---|
| CHO | MDCK |
| 293 | BRL |
| BHK | Hela |
| TM4 | Vero |
| HTC | W138 |
| COS | CV1 |
| HepG2 | |
| TR1 | |

As discussed above deletion of the Ig variable region intron and donor and acceptor sites, while maintaining the other control regions, resulted in elimination of transient expression of factor VIII. From this data at least one splice donor-intron-acceptor sequence appears to be required for expression.

Additional experiments indicate that location of the stabilizing sequence is important. For example location of an intron 3' to the cDNA encoding factor VIII failed to express factor VIII. Vectors which were constructed to include native factor VIII splice sites, i.e. splice sites within the coding region, also proved unsuccessful. The splice donor-acceptor arrangement containing the CMV splice donor sequence and a chimeric intron comprising CMV sequences and the synthesized Ig variable region intron and acceptor is an example of a stabilizing sequence which will lead to the establishment of a cell line providing continuous production of factor VIII.

EXAMPLE 5

Expression Vector Variant Factor VIII

One approach to achieve a more efficient protein is protein engineering. That is, by introducing changes within the gene at the DNA level, variants can be produced in cell culture to allow for specific modification in protein function. Three variants were engineered. The native factor VIII single chain 300,000 dalton protein is cleaved to subunits of 90,000 and 80,000 dalton which in turn are cleaved to the active subunits of 50,000, 43,000 and 73,000 dalton. The B domain between amino acid 742 through 1648 has no defined function. Vehar, G. A. et al., Nature 312, 330–337 (1984). The same cell systems described for expression of the full length recombinant factor VIII protein were used to express the mutant.

pF8CIS9080

The eukaryotic expression vector used to express the factor VIII fusion protein included: the enhancer (Boshart et al., supra), and promoter (Thomsen et al., supra) of the human cytomegalovirus (CMV) immediate early gene; the splice donor sequence located 3' of the transcription initiation site of this gene (Boshart et al., supra, Stenberg et al., supra); and a synthetic splice acceptor site from the mouse immunoglobulin variable region (Bothwell et al., supra). The new coding region is flanked on the 3' end by the SV40 early polyadenylation sequence and transcription termination site (Fiers et al., supra). The vector includes an amplifiable marker, the SV40-DHFR transcription unit.

Figure 4:
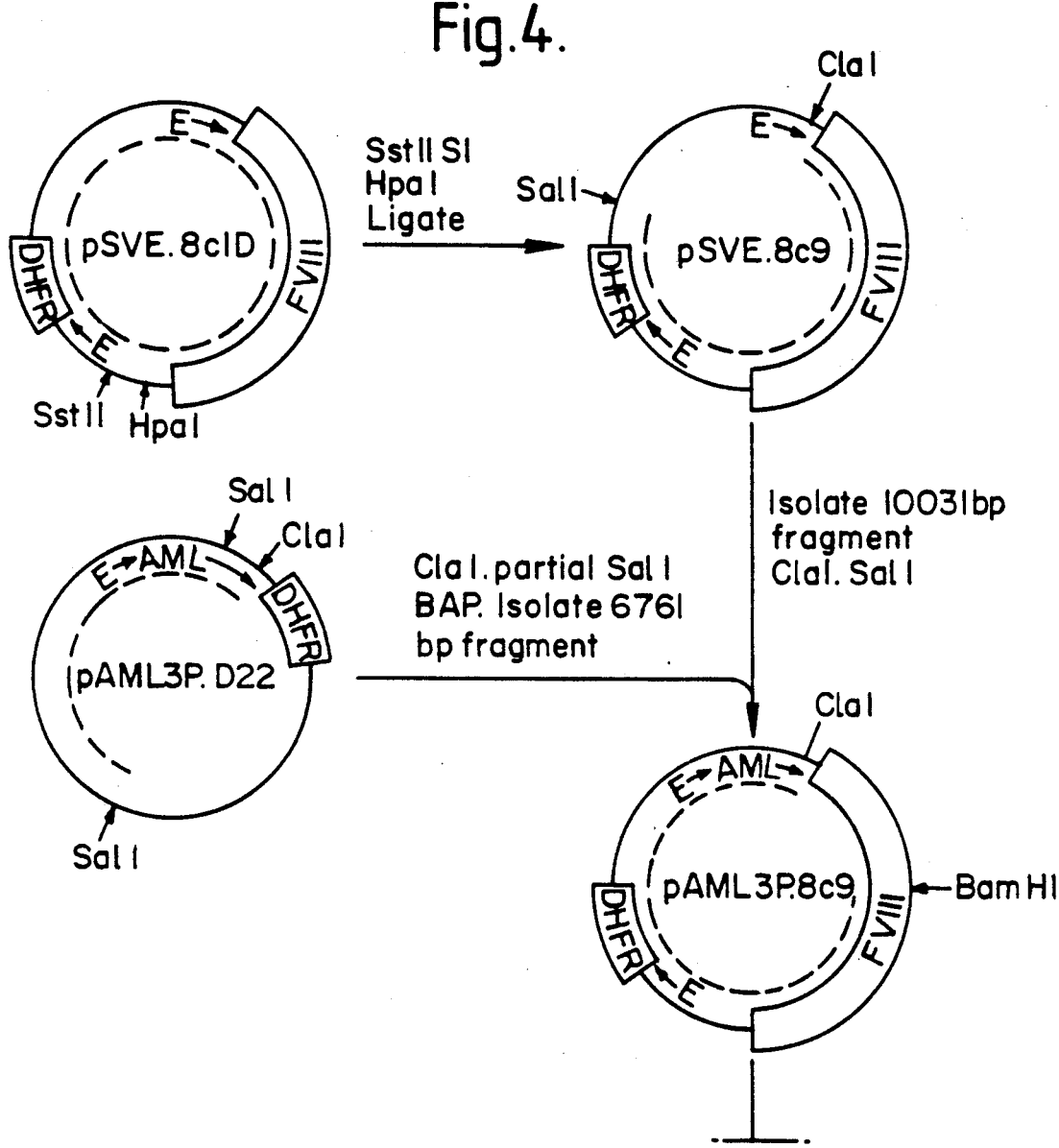
FIG. 4 Construction of a factor VIII variant expression vector used to establish production cell lines for the factor VIII variant, pF8CIS9080.
Figure 4:
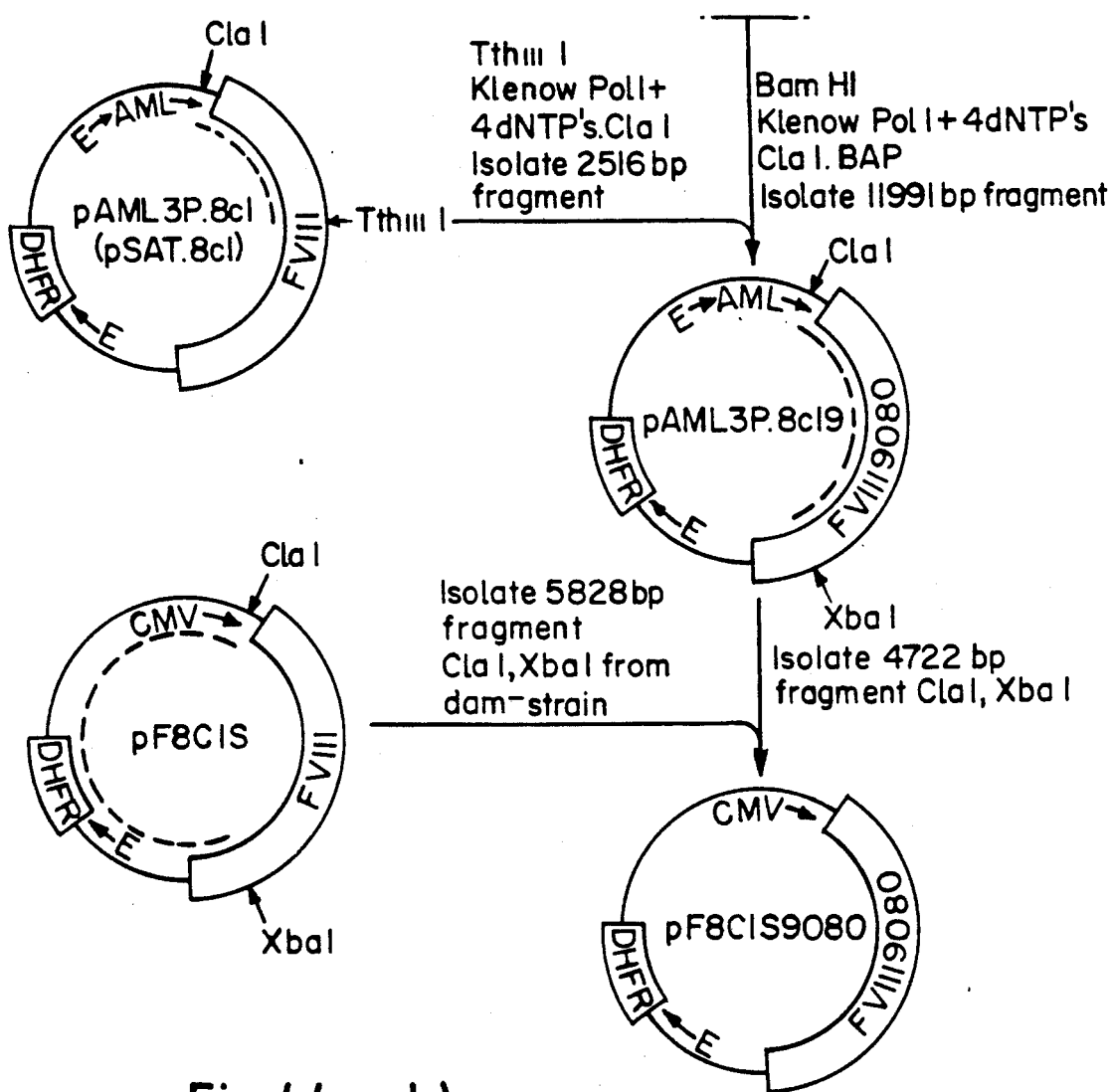
Figure 5:
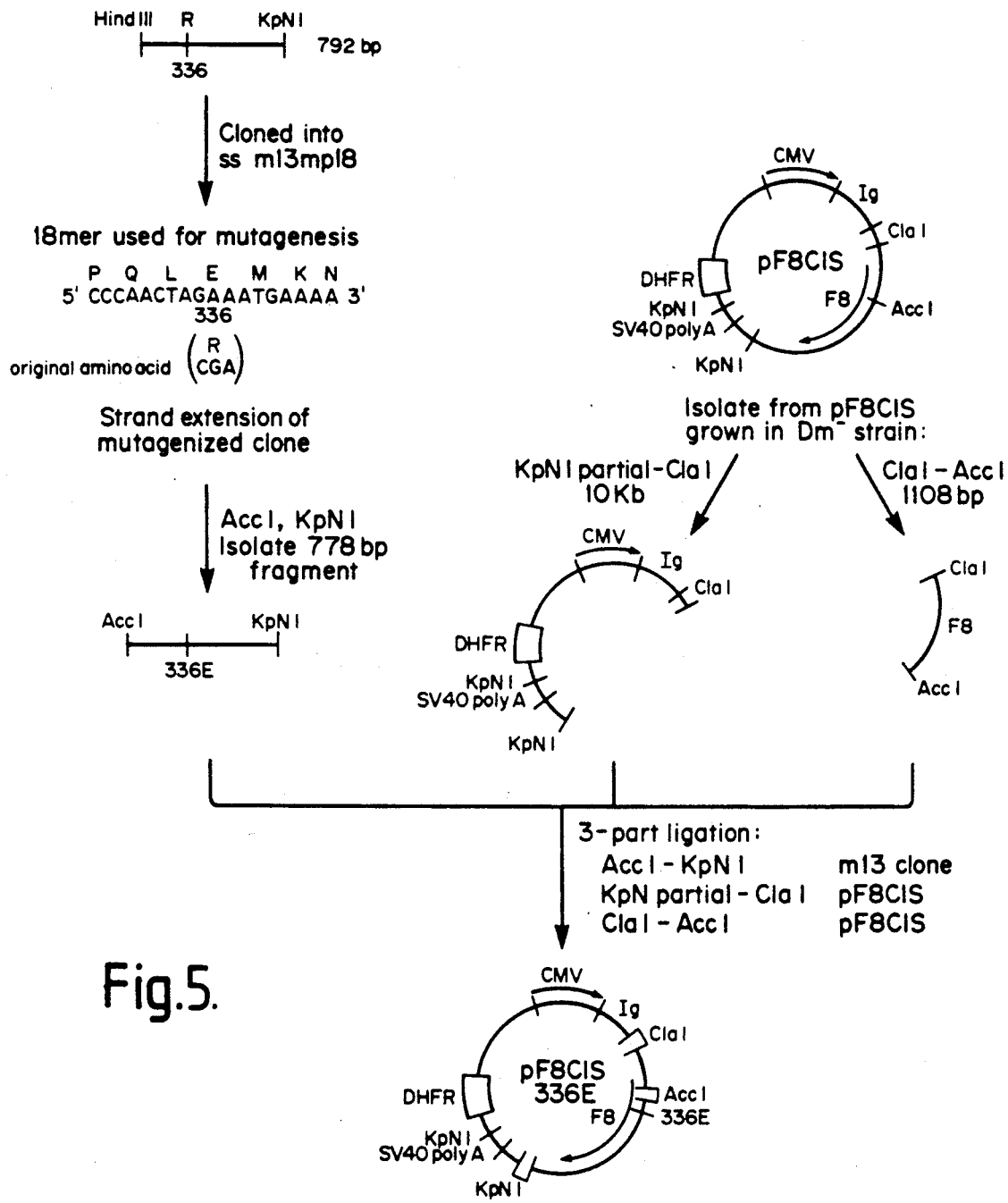
FIG. 5 Construction of an expression vector containing a cDNA encoding factor VIII resistant to proteolytic cleavage by activated protein C. pF8CIS-336E.

Construction of the expression vector, pF8CIS9080, encoding the factor VIII fusion protein 90 kd+142 aa+80 kd is shown in FIG. 4. Starting with the plasmid pSVE.8cID (European Patent Publication No. 160,457), a short deletion was made in the 3' untranslated region by cutting with SstII, blunting the cohesive ends with S1, further cleaving with HpaI and religating the two blunt ends to generate pSVE.8c9. This plasmid was cleaved with ClaI and SalI and the 10031 bp fragment cloned in the SalI, ClaI. A 6761 bp promoter containing fragment of pAML3P.D22 (European Patent Publication No. 160,457). The fusion in the factor VIII gene was made by ligating the filled in TthlII I and BamHI (amino acid 1563) sites within the factor VIII gene. FIG. 5 shows ligation of a 2516 bp fragment of pAML3P.8cl (European Patent Publication No. 160,457) and a 11991 bp fragment of pAML3P.8c9 to construct pAML3P.8L19 containing the fused region. This fusion was confirmed by DNA sequence. A 4722 bp ClaI-XbaI fragment containing the fusion region was cloned into a 5828 bp ClaI-XbaI fragment of pF8CIS containing the CMV promoter-enhancer expression vector. The CMV fragment was obtained from a dam⁻ strain of *E. coli* where methylation does not prevent cutting at the ClaI site.

EXAMPLE 6

Expression Results

The method described in Example 4 was applied to expression of the factor VIII variant which deleted nucleotides 796 through 1562, pF8CIS9080. The 90 kd+142 aa+80 kd fusion protein is expressed at higher levels than the full length protein. However there remains considerable variation between cell types as to the capability of expressing the fusion protein.

The following data demonstrates that the choice of a proper host cell will provide continuous production of the desired fusion protein in commercially useable quantities. TM4 cells transfected with pF8CIS9080 showed both transient and stable expression of the fusion protein. TM4 cells transfected with pF8CIS9080 showed a five-fold increase in the levels of the fusion protein as compared to the full length factor VIII. At 100 nM methotrexate pooled clones of the fusion factor VIII yielded 12 mU/$10^4$ cells/day. HTC cells showed a similar enhancement in expression of the fusion factor VIII as compared to the full length factor VIII.

Expression of the fusion protein factor VIII is quite high in 293 cells as compared to full length factor VIII expression. In 293 cells transformed with the fusion protein vector pF8CIS9080 the unamplified population levels of 85 mU/$10^4$ cells/day were routinely achieved. Expression levels of full length factor VIII were lower than the fusion factor VIII yielding 2.5 mU/$10^4$ cells/day. Since the control signals are identical in the pF8CIS and pF8CIS9080, the difference in expression levels must lie within the capability of the cell to produce full length message and/or protein.

EXAMPLE 7

Expression Vector of Factor VIII Variant Resistant to Activated Protein C

Activated protein C (APC), a plasma protein, has been shown to inactivate human factor VIII by limited proteolysis. One possible site of this inactivation cleavage is at arginine at position 336. The arginine at position 336 can be changed to another amino acid, for example, lysine or glutamic acid. Two vectors, pF8CIS336E and pF8CIS9080-336E, were constructed to determine whether position 336 was a site of inactivation. Using in vitro mutagenesis (Norris, K. et al., Nucleic Acids Research, 11, 5103–5112 [1983]) the arginine at position 336 was mutated to a glutamic acid (FIG. 5). For the mutagenesis a 792 bp HindIII-KpnI fragment from pF8CIS was inserted into the HindIII-KpnI sites of m13. The 18 bp oligomer shown below was used to mutagenize this fragment.

```
        P  Q   L   E   M   K   N
     5' CC CAA CTA GAA ATG AAA A 3'
                    *
```

Following strand extension the double stranded mutagenized M13 clone was cut with AccI and KpnI. A 778 bp fragment was gel purified. The plasmid pF8CIS was grown in a dam⁻ strain of *E. coli*, GM48. Due to the sequence of the PstI-ClaI linker shown in FIG. 1, the ClaI site of pF8CIS will not cut if the plasmid is grown in a methylation plus strain of bacteria as discussed above. Two fragments were isolated from the dam⁻ pF8CIS DNA, a 10 kb KpnI partial-ClaI fragment and a 1108 bp ClaI-AccI fragment. A three part ligation was required to replace the native factor VIII sequence with the mutagenized sequence, See FIG. 5.

Figure 6:
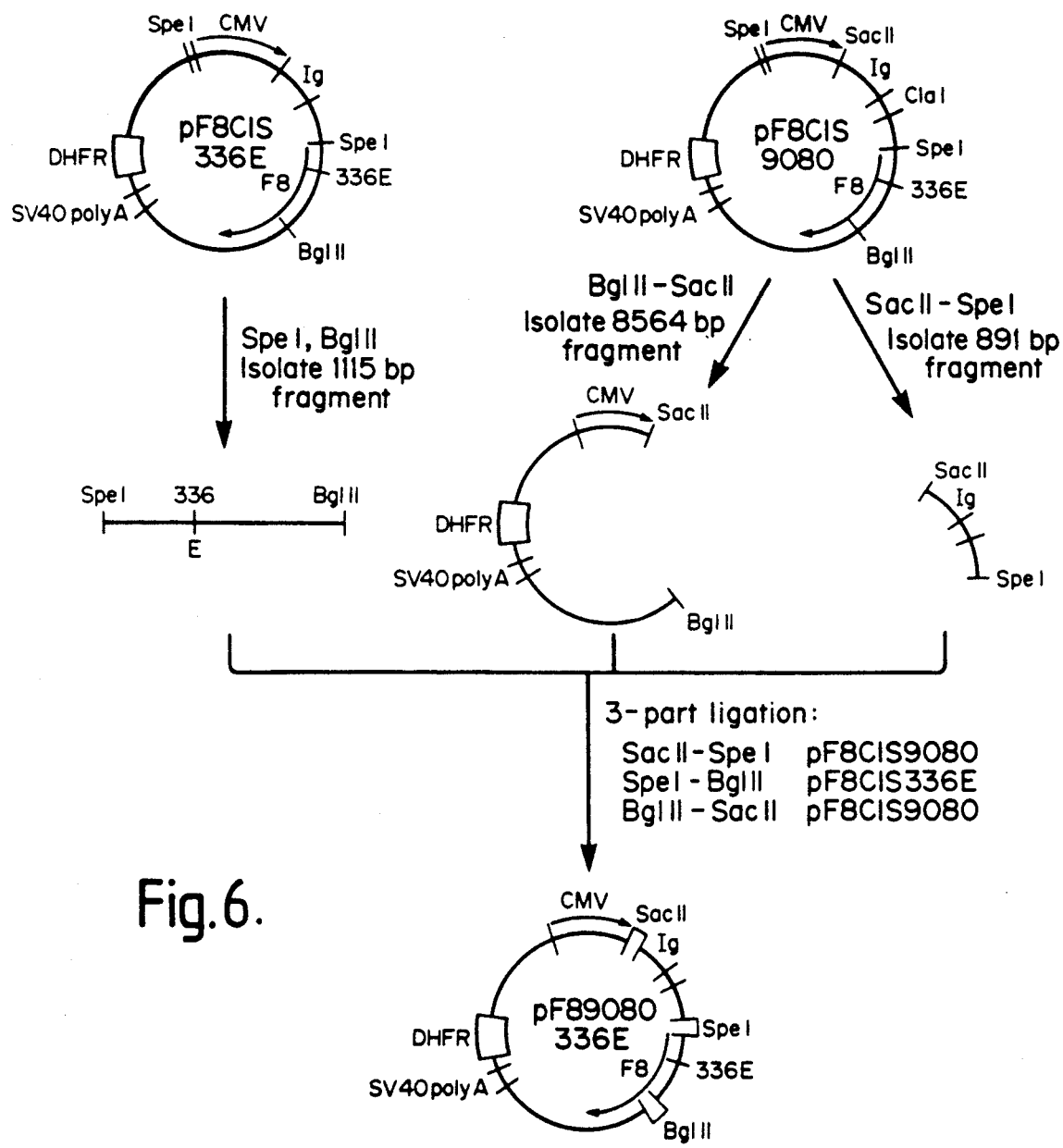
FIG. 6 Construction of an expression vector containing a cDNA encoding a fusion protein of factor VIII resistant to proteolytic cleavage by activated protein C. pF89080-336E.

Construction of pF89080-336E proceeded via another three part ligation as shown in FIG. 6. A 1115 bp SpeI-BglII fragment containing the 336E variant amino acid was transferred to create another variant fusion protein by ligation to a 891 bp SacII-SpeI fragment and a 8564 bp BglII-SacII fragment isolated from pF8CIS9080.

Both of these protein variants were expressed in 293 cells. Full length factor VIII with this mutation was expressed at 2.8 mU/$10^4$ cells/day while the fusion variant was expressed at 15 mU/$10^4$ cells/day.

EXAMPLE 8

Expression Vector Prorelaxin

1. pCIHRX

Figure 7:
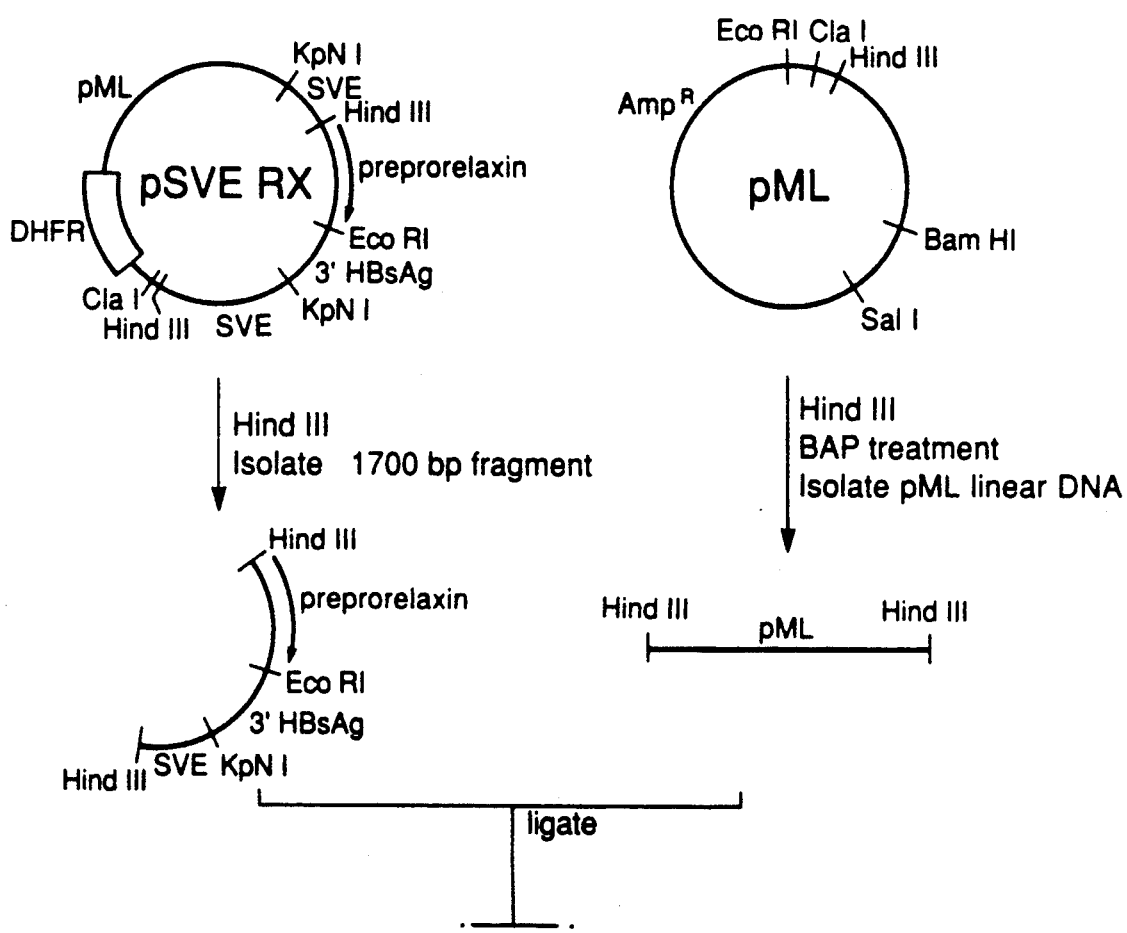
FIG. 7 Construction of a prorelaxin expression vector used to establish production cell lines for prorelaxin. pCIHRX.
Figure 7:
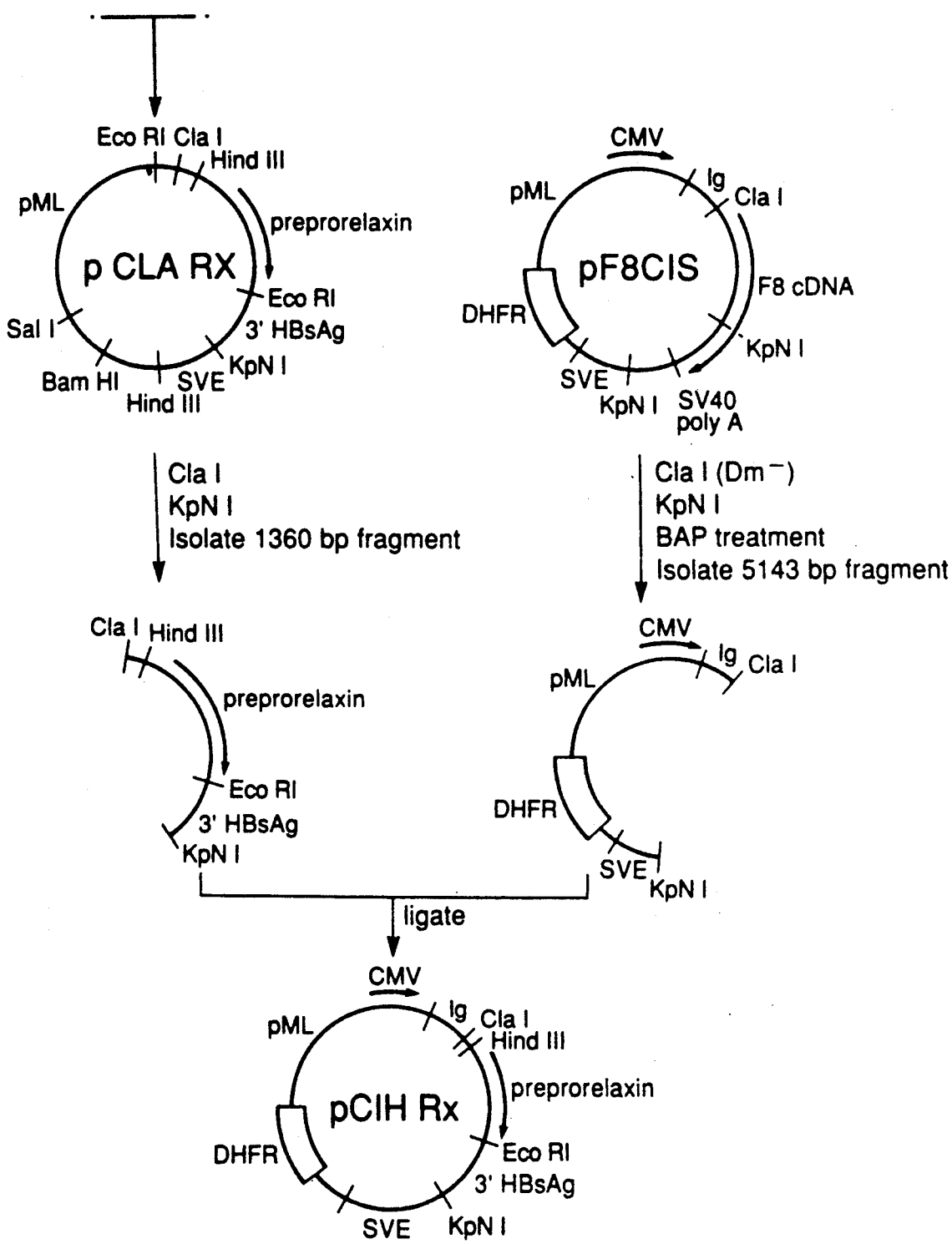

The vector pCIHRX contained the cytomegalovirus enhancer and promoter, the cytomegalovirus splice donor site, the Ig variable region splice acceptor site, the cDNA encoding H2 preprorelaxin and the hepatitis surface antigen polyadenylation and transcription termination sites. FIG. 7 shows the steps for construction of the prorelaxin vector. The same intron and splice acceptor sequence described previously from the Ig variable region was maintained. 677 bp of the pre-prorelaxin cDNA followed these 5' processing signals. While the 5' control signals were identical to pF8CIS the polyadenylation region and termination sequence signals were from the hepatitis surface antigen gene rather than SV40.

An intermediate plasmid pClaRX was first constructed. The plasmid pSVERX (see copending U.S. patent application Ser. No. 6/907,297, filed Sept. 12, 1986) was cut with HindIII to isolate a 1700 bp fragment containing the pre-prorelaxin cDNA followed by the hepatitis B surface antigen (HBsAg) 3' polyadenylation site. A KpnI site was 3' to the HBsAg polyadenylation site and 5' to the start of the SV40 early promoter which in this vector was used to drive expression of the DHFR cDNA.

This HindIII fragment was inserted into pML linearized at the HindIII site. Reclosures were minimized by treatment with bacterial alkaline phosphatase (BAP). Ampicillin resistant colonies were screened to isolate clones which had inserted the pre-prorelaxin gene so that the 5' end of the gene was next to the ClaI site of pML.

The intermediate plasmid pClARX was cut with ClaI and KpnI to isolate a 1360 bp fragment containing the pre-prorelaxin gene followed by the hepatitis surface antigen 3' polyadenylation sequences. This fragment was ligated to the 5143 bp fragment created by cutting pF8CIS dam⁻ with ClaI and KpnI.

2. pCISRX

Figure 8:
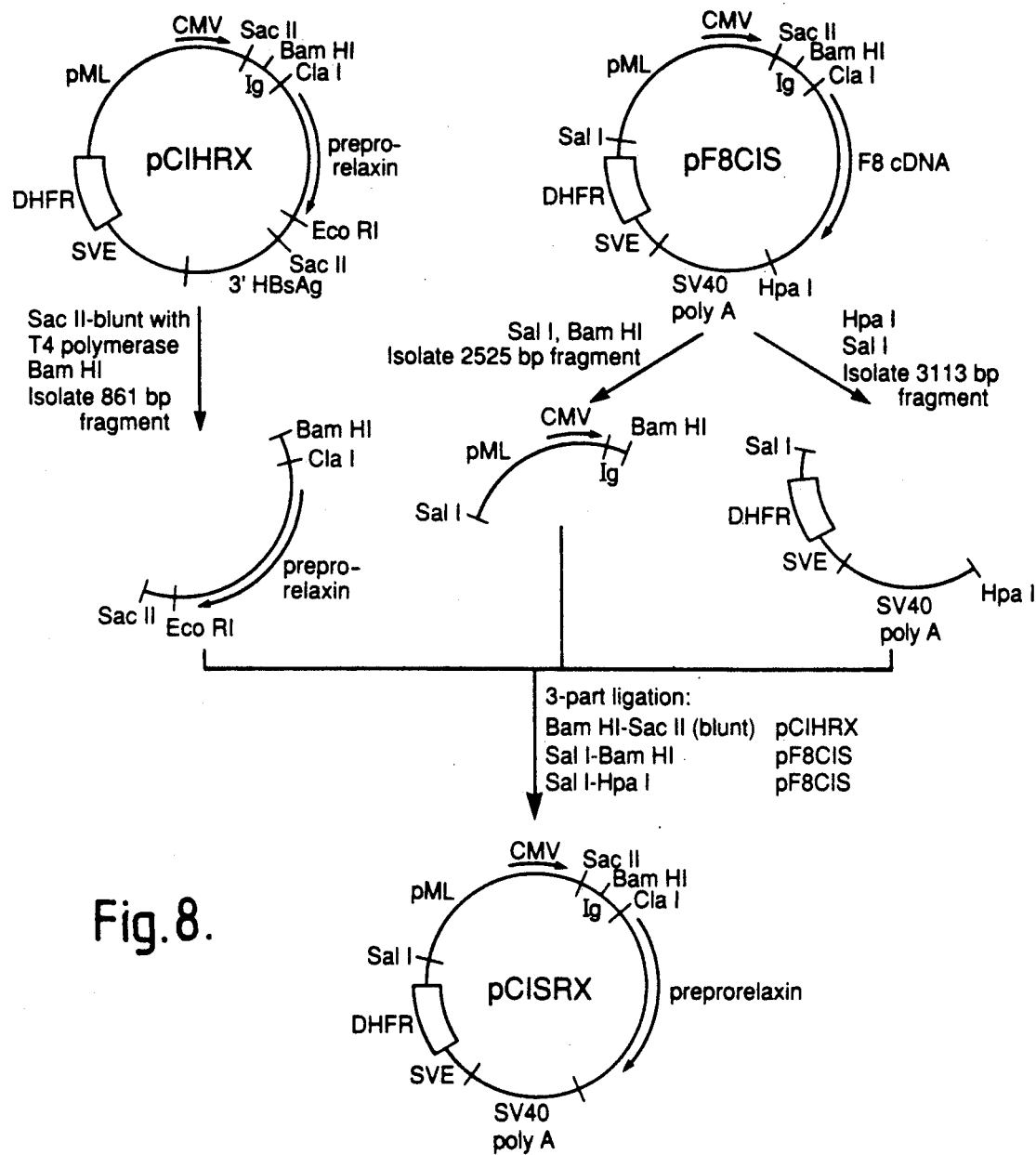
FIG. 8 Construction of a prorelaxin expression vector used to establish production cell lines for prorelaxin. pCISRX.

Because the choice of polyadenylation sequences is known to influence 5' processing of messenger RNA (Wilson & Nevins, supra), the 3' hepatitis polyadenylation sequence in pCIHRX was replaced with the pSV40 polyadenylation sequence. The steps for construction of pCISRx is shown in FIG. 8. The two starting vectors for this construction are pCIHRX and pF8CIS. The latter vector has the same 5' controls as pCIHRX but includes the cDNA for factor VIII and the SV40 polyadenylation site. SacII was used to cleave 3' of the cDNA. The resultant 3' overhang was blunted by T4 polymerase. pCIHRX was then cut with BamHI. This site separates the chimeric intron from the 5' end of the relaxin gene. An 861 bp fragment was gel isolated from the BamHI treatment. The SV40 polyadenylation site, DHFR, transcription unit, bacterial origin of replication and amp$^r$ gene, as well as the CMV enhancer and promoter and splice donor were isolated from pF8CIS. These elements were isolated in two fragments, as a 2525 bp SalI-BamHI fragment and a HpaI-SalI 3113 bp fragment. A three part ligation of the BamHI-SacII (blunted) fragment with the HpaI-SalI fragment and SalI to BamHI fragment yields pCISRX.

EXAMPLE 9

Expression Prorelaxin

The expression capabilities of the two relaxin expression vectors pCIHRX and pCISRX, were assayed using several anti-relaxin antibodies in the immunoperoxidase method described above. Three rabbit polyclonals and three mouse monoclonal antibodies were tested on COS cells transfected with pSVERX. One monoclonal RX-I was found to give intense staining with no background.

The two vectors of this invention, pCIHRX and pCISRX, were tested for prorelaxin expression and compared to pSVERX. pCIHRX and pCISRX vectors differed in the polyadenylation sequence. pCIHRX contained the hepatitis surface antigen polyadenylation sequence while pCISRX contained the SV40 early region polyadenylation sequence.

293, TM4 and CHO cells were transfected with 10 μg total DNA which included 1 μg pRSVneo, 5 μg salmon sperm carrier and 4 μg of plasmids pSVERX, pCIHRX and pCISRX. Cells were glycerol shocked as described above. Thirty-six hours following transfection cells were fixed and stained with IH6 to identify transformed cells making prorelaxin. Positive staining cells were seen in 293 and TM4 cells transfected with pCIHRX and pCISRX. Duplicate plates of CHO, 293 and TM4 cells were split and subjected to the staining protocol described above to screen for prorelaxin production cells.

Expression results are shown in the tables below indicating that the vectors containing the stabilizing sequence 5' of the DNA encoding prorelaxin produced significantly higher levels of prorelaxin than the reference plasmid, pSVERX. In the case of stable expression the media assay for prorelaxin was from the general population of cells.

| Cell Type | Transient Expression Prorelaxin | |
|---|---|---|
| | Plasmid | Amount of Protein (ng/ml) |
| CHO | pSVERX | 0.4 |
| | pCIHRX | 0.9 |
| | pCISRX | 3 |
| TM4 | pSVERX | 0.4 |
| | pCIHRX | 2 |
| | pCISRX | 10 |
| 293 | pSVERX | 0.4 |
| | pCIHRX | 100 |
| | pCISRX | 200 |

EXAMPLE 10

Expression Vector t-PA

1. pCIHt-PA

The vector pCIHt-PA containing the cytomegalovirus enhancer and promoter, the cytomegalovirus splice donor site and intron, the Ig variable region splice acceptor site, the cDNA encoding t-PA (Pennica et al., Nature 301, 214 (1983)) and the hepatitis surface antigen polyadenylation and transcription termination site was constructed.

Figure 9:
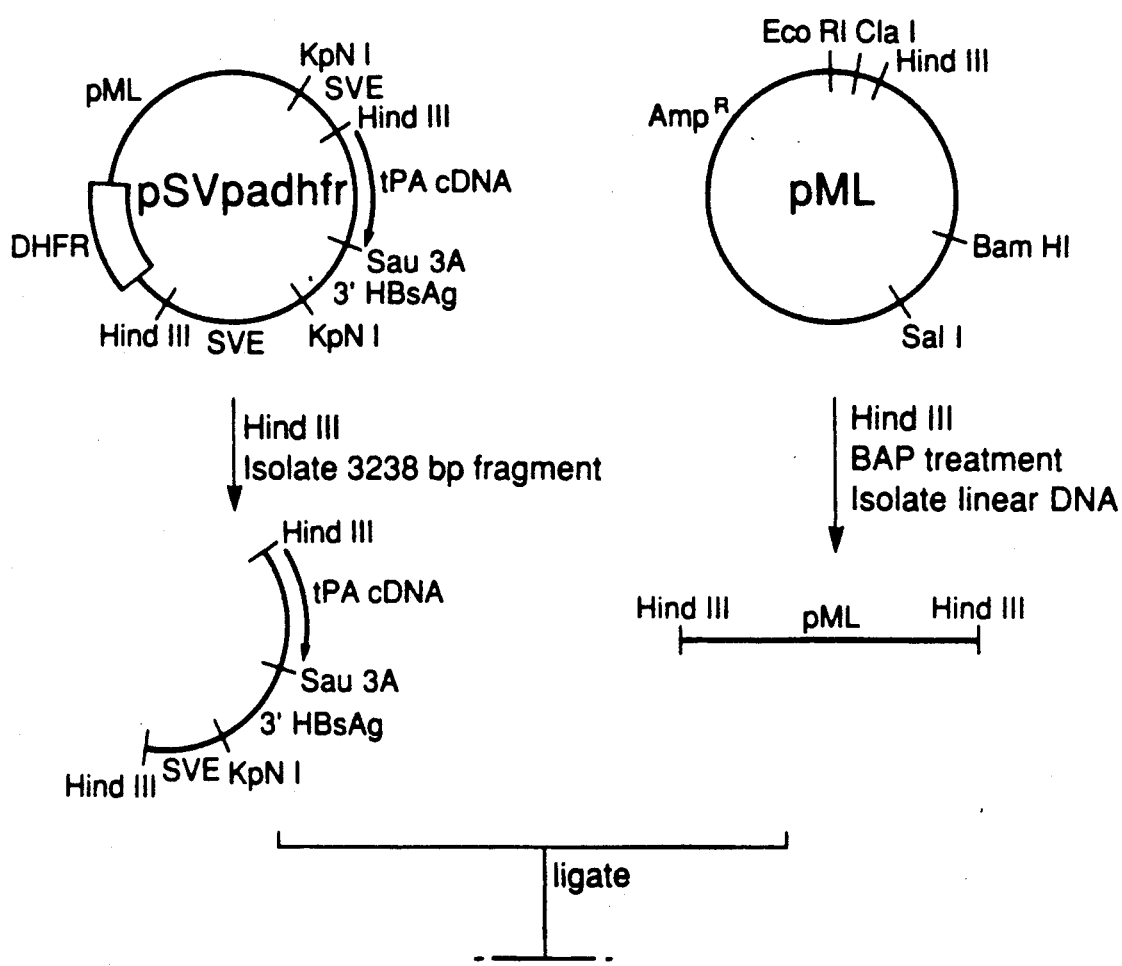
FIG. 9 Construction of a t-PA expression vector used to establish production cell lines for t-PA. pCIHt-PA.
Figure 9:
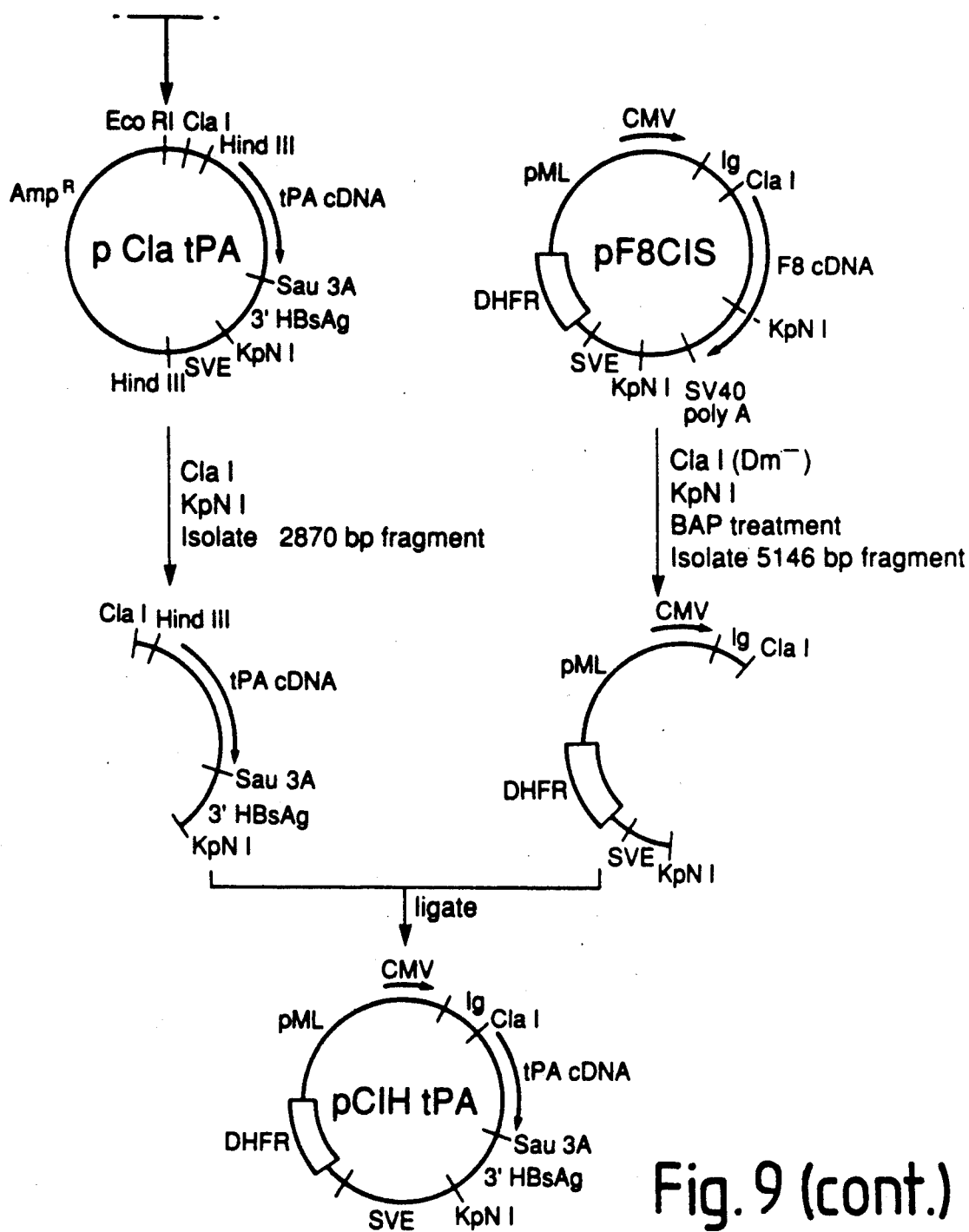

FIG. 9 shows the steps for construction of the t-PA vector.

The t-PA cDNA was first cloned into pML to provide a ClaI site at the 5' end of the gene. To do this a 3238 bp HindIII fragment from pSVpa-DHFR (otherwise referred to as pETPFR in UK patent 2,119,804 B) was inserted into the HindIII site of pML. Colonies were screened for clones which have the 5' end of the cDNA juxtaposed to the ClaI site. The intermediate plasmid labelled pCLAt-PA is shown in FIG. 9. A t-PA cDNA followed by the 3' polyadenylation region was isolated as a ClaI-KpnI fragment of 2870 bp. This fragment was ligated to the 5146 bp fragment of pF8CIS. This ClaI-KpnI fragment of the CIS vector provided the 5' control region, a SV40-DHFR transcriptional unit, the ampicillin resistance gene and origin region from pML. pCIHt-PA is analogous to pCIHRX, discussed above, with the exception of the cDNA coding for the desired heterologous gene.

Expression levels of t-PA were compared by transfecting CHO and 293 cells with pSVpaDHFR, pCMVt-PA and pCIHt-PA. The former two vectors did not contain a stabilizing sequence and thus served as controls for the vector pCIHt-PA containing the cDNA encoding t-PA constructed in accord with the instant invention. Media from each of the cultured transformed 293 cells were assayed and the following results were obtained: pSVpaDHFR gave 30 ng/ml; pCMVt-PA gave 200 ng/ml of t-PA; and pCIHt-PA gave 420 ng/ml of t-PA.

2. pCISt-PA

The vector pCISt-PA containing the cytomegalovirus enhancer and promoter, the cytomegalovirus splice donor site and intron, the Ig variable region splice acceptor site, the cDNA encoding t-PA and the pSV40 polyadenylation sequence was constructed.

Figure 13:
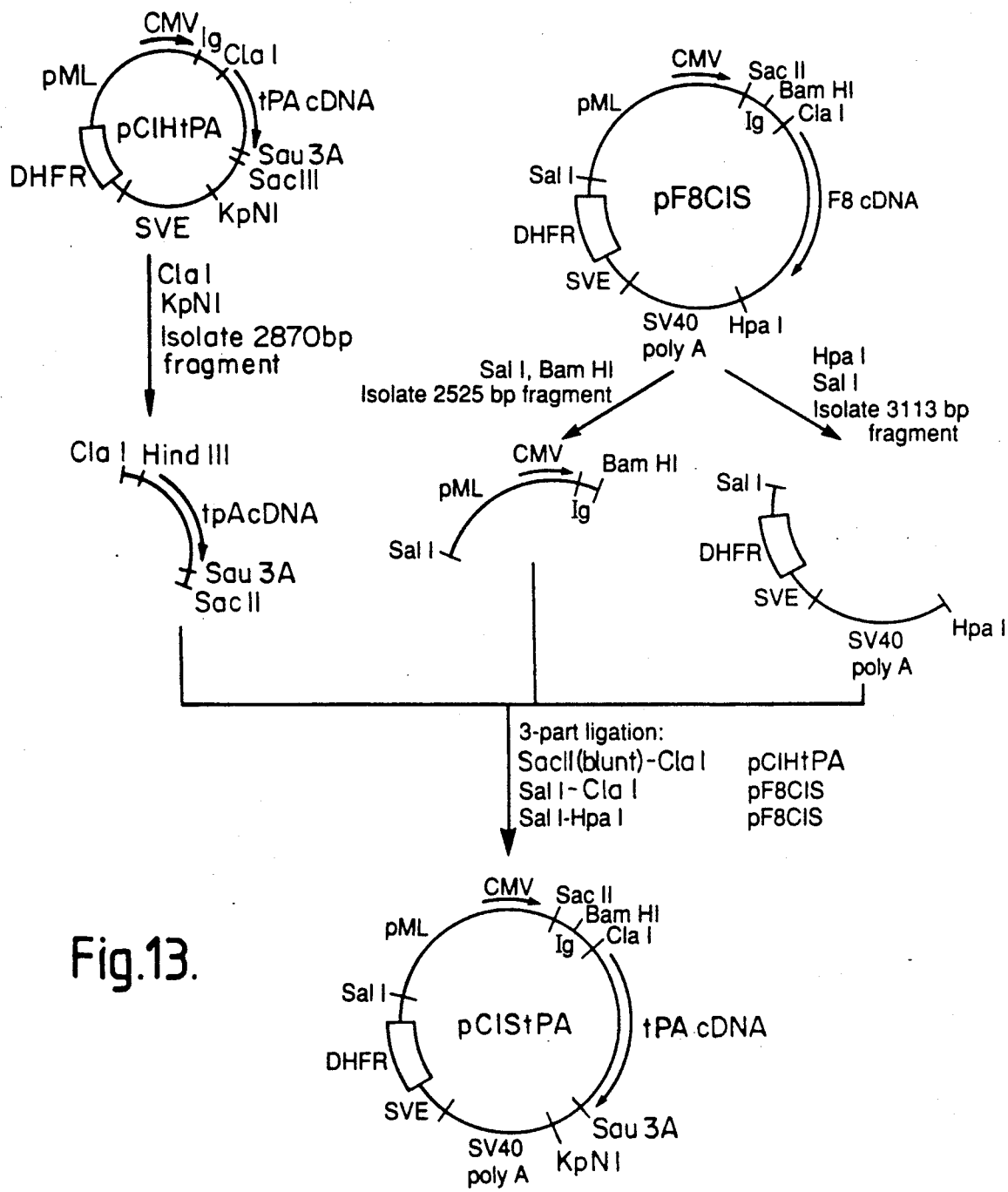
FIG. 13 Constructions of a t-PA expression vector used to establish production cell lines for t-PA. pCISt-PA.

The starting vectors for this construction are pCIHt-PA and pF8CIS (see FIG. 13). The latter vector has the same 5' controls as pCIHt-PA but includes the cDNA for factor VIII and the SV40 polyadenylation site. SacII was used to cleave 3' of the t-PA cDNA. The resultant 3' overhang was blunted by T4 polymerase. pcIHt-PA was then cut with ClaI. This site separates the chimeric intron from the 5' end of the t-PA gene. A 2870 bp fragment was gel isolated from the ClaI treatment. The SV40 polyadenylation site, DHFR, transcription control, bacterial origin of replication and amp$^r$ gene, as well as the CMV enhancer and promoter and splice donor were isolated from pF8CIS. These elements were isolated into fragments as a 2525 bp SalI-ClaI fragment and a HpaI-SalI 3113 fragment. A three part ligation of the SacII(blunt)-ClaI fragment with the HpaI-SalI fragment and SalI-ClaI fragment yields pCISt-PA.

Expression levels of t-PA were compared by transfecting 293 and CHO cells with pCIHt-PA and pCISt-PA. Media from each of the cultured transformed cells were assayed and the following results were obtained:

|     |     | Transient (t-PA ng/ml) |
| --- | --- | --- |
| CHO | CIS | 55 |
|     | CIH | 15 |
| 293 | CIS | 3000 |
|     | CIH | 1300 |

EXAMPLE 11

Transient Expression of Production Levels of Protein

Given the high levels of CAT activity produced by the CMV driven CAT vectors in 293 cells, we used this system to produce useful amounts of desired heterologous proteins within a few days of transfection. Transient levels of protein production were manipulated using two parameters. Increased plasmid copy number in the 293 and 293s cells was accomplished by increased replication. Adenovirus VA RNA genes, a translational control effector, was used to increase translation of message encoding a desired protein in these cells. (Thimmappaya, B. et al., supra, 1982).

Based on expression data in Cos7 cells and CV1 cells experiments were carried out to increase expression by increasing copy number. SV40 origin containing plasmids are known to replicate to high copy number in 293 cells. (Lebokowski, J. S. et al., Nature 317, 169 [1985]; Lewis, E. D. and Manley, J., Nature 317, 172 [1985]). During replication of SV40 vectors in 293 cells very little transcription occurrs from the SV40 early promoter. We investigated whether control of replication and transcription could be separated leading to a useful replicative expression system in 293 cells. Our results confirmed that when transcription is linked to replication using the SV40 early promoter transcription did not occur and very little protein was detected. This was true for vectors which used the SV40 promoter-origin region regardless of the enhancer used. Neither the SV40-SV40 nor the CMV-SV40 vectors described above yielded measureable levels of protein when cotransfected with pRSVTs. Very high plasmid copy number was easily achieved in these cotransfections but without expression of protein. However, when the SV40 origin of replication was separated from the site of transcription such as in the vectors pCIShGH or pCIS5hGH, plasmid copy increased and expression of hGH was easily detected. Table 5 shows a comparison of expression of hGH in CV1 and 293 cells with and without replication. These data describe the high levels of hGH protein produced in a few days post transfection. By day 3, 10–15 micrograms/ml of hGH is expressed in the media of the 293 cells. While the time course and upper limit of expression is a little different in the presence of T antigen in this experiment, these high levels of protein production are not dependent on replication in the 293 cells. In the CV1 cells the highest titer of hGH achieved is 2 micrograms/ml and this level of expression is linked to T antigen dependent replication. Analysis of Southern blots of Hirt extracted DNA made from the 293 cells shows that the amount of plasmid DNA has greatly increased due to replication. However, the high level of protein production appears to plateau rather than increase with this increased copy number.

TABLE 5

| Comparison of Expression with T Antigen Cotransfection | | | |
|---|---|---|---|
| Cell Type | Day | −T | +T |
| CV1 | 1 | 250 | 500 |
|  | 2 | 800 | 2000 |
|  | 3 | 150 | 300 |
| 293s | 1 | 320 | 460 |
|  | 2 | 5600 | 10000 |
|  | 3 | 10000 | 15000 |

Experiments were carried out to determine whether 293 cells were saturated with an amount of DNA which could be transcribed. The increased stability of the transfected DNA with the vectors of this invention could account for the DNA saturation. The amount of total DNA needed to saturate transfection efficiency in various cell types was studied. All the cell lines described herein required 10 micrograms/ml of precipitate of total DNA for optimal expression. The 293 and 293s cells did not differ from other cell types in this basic level of DNA needed for successful transfection. However, only a small amount of this 10 micrograms/ml needs to be hGH specific DNA for saturation of hGH production. Table 6 shows that high levels of hGH are produced when 293s cells are transfected with only 0.6 micrograms of the total 10 micrograms being the pCIShGH vector. At this level of DNA 4.5 micrograms/ml of hGH were secreted two days post transfection. Since the input DNA is so stable in the 293 cells, relatively little DNA is required for a continued saturation of expression levels.

TABLE 6

| Influence of DNA Concentration on Expression Levels of hGH | | | | | |
|---|---|---|---|---|---|
| Amount of DNA (micrograms) | 0.2 | 0.6 | 1 | 5 | 10 |
| Day 1 | 98 | 200 | 280 | 460 | 1380 |
| Day 2 | 690 | 4200 | 5100 | 5600 | 4500 |

Experiments were carried out to increase the amount of protein produced transiently by cotransfecting with the VA RNA genes of adenovirus. It has been shown that in transient transfections, especially in 293 cells, translation of transiently produced RNA can be facilitated by the addition of these genes. In Table 7 we show that indeed the hGH levels can be increased from 10 micrograms/ml to 19 micrograms/ml by the addition of the VA RNA genes. The optimal amount of VA RNA DNA needed to reach this level of expression was 5 micrograms/ml of precipitate. This upper limit of hGH expression seen by cotransfection of the VA RNA genes is similar to the highest levels of hGH produced in the presence of T antigen. Interestingly the effects of T antigen and the VA RNA genes were found not to be additive. The amount of protein produced by this transient system is sufficient to allow analysis of mutant proteins a few days post transfection. Similar experiments were carried out with factor VIII variants and t-PA as seen in Table 7.

TABLE 7

| Effect of VA RNA on Expression | | | |
|---|---|---|---|
| Desired Heterologous | Day | | |
| Protein | 2 | 3 | 5 |
| Factor VIII 90-142-80 | 70 | 350 | 1200 |
| +VA RNA | 150 | 500 | 2000 |
| tPA | 200 | 600 | |

TABLE 7-continued

| Effect of VA RNA on Expression | | | |
|---|---|---|---|
| Desired Heterologous | Day | | |
| Protein | 2 | 3 | 5 |
| +VA RNA | 600 | 1200 | |
| hGH | 10000 | 5600 | |
| +VA RNA | 19000 | 12000 | |
| Factor VIII assays mU/ml | | | |
| tPA and hGH ng/ml | | | |

I claim:

1. A method for the enhanced transient expression of a desired protein in a host kidney cell comprising:
   a) providing a host kidney cell which expresses an adenovirus trans-activating protein;
   b) transfecting said host kidney cell with a vector comprising DNA encoding the desired protein under the control of a cytomegalovirus promoter; and,
   c) culturing said host kidney cell for a period comprising 1 to 14 days under conditions favorable for transient production of the desired protein.

2. The method of claim 1 wherein said adenovirus trans-activating protein is Elb.

3. The method of claim 1 further comprising the presence of T antigen.

4. The method of claim 1 wherein said adenovirus trans-activating protein is Ela.

5. The method of claim 1 wherein said adenovirus trans-activating protein is a mixture of Ela and Elb.

6. The method of claim 1 wherein said cytomegalovirus promoter is from the immediate early gene of human cytomegalovirus.

7. The method of claim 1 wherein said host kidney cell is a human embryonic kidney cell.

8. The method of claim 7 wherein said human embryonic kidney cell is 293.

9. The method of claim 7 wherein said human embryonic kidney host cell is JW2.

10. The method of claim 7 which includes under step b) the additional step b)1) transfecting said host kidney cell with a vector producing a translational control effector.

11. The method of claim 10 wherein the translational control effector is VA RNA.

12. The method of claim 1 wherein said step b) further comprises downstream from said cytomegalovirus promoter a stabilizing DNA sequence.

13. A host kidney cell wherein said host kidney cell endogenously produces an adenovirus trans-activating protein and is transformed by transfecting said host kidney cell with a vector comprising DNA encoding said protein under the control of a cytomegalovirus promoter.

14. The host kidney cell of claim 13 that is a human embryonic kidney cell.

15. The host human embryonic kidney cell of claim 14 that is derived from JW2.

16. The host human embryonic kidney cell of claim 14 that is derived from 293.

17. In a method for production of a host kidney cell capable of production of a desired heterologous protein, wherein said host kidney cell endogenously produces an adenovirus trans-activating protein, the improvement comprising transfecting said host kidney cell with a vector comprising DNA encoding said desired protein under the control of a cytomegalovirus promoter.

18. The method of claim 17 wherein said adenovirus trans-activating protein is Ela.

19. The method of claim 17 wherein said adenovirus trans-acting protein is Elb.

20. The method of claim 17 wherein said adenovirus trans-activating protein is a mixture of Ela and Elb.

21. The method of claim 17 wherein said kidney cell is a human embryonic kidney cell.

22. The method of claim 21 wherein said human embryonic kidney cell is the 293 cell line.

23. The method of claim 21 wherein said human embryonic kidney cell is the JW2 cell line.

24. The method of claim 17 wherein said cytomegalovirus promoter is an immediate early promoter.

25. The method of claim 24 wherein said immediate early promoter is the human immediate early promoter of human cytomegalovirus.

26. The method of claim 17 further comprising the additional step of transfecting with a vector producing a translational control effector.

27. The method of claim 26 wherein said translational control effector is VA RNA.

* * * * *